(12) United States Patent
Harris et al.

(10) Patent No.: US 9,447,143 B2
(45) Date of Patent: *Sep. 20, 2016

(54) PEPTIDE FRAGMENTS FOR INDUCING SYNTHESIS OF EXTRACELLULAR MATRIX PROTEINS

(71) Applicant: HELIX BIOMEDIX, INC., Bothell, WA (US)

(72) Inventors: Scott M. Harris, Seattle, WA (US); Timothy J. Falla, Woodinville, WA (US); Lijuan Zhang, Kenmore, WA (US)

(73) Assignee: HELIX BIOMEDIX INC., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/531,081

(22) Filed: Nov. 3, 2014

(65) Prior Publication Data

US 2015/0094270 A1    Apr. 2, 2015

Related U.S. Application Data

(60) Continuation of application No. 13/961,782, filed on Aug. 7, 2013, now Pat. No. 8,962,798, which is a continuation of application No. 13/339,606, filed on Dec. 29, 2011, now Pat. No. 8,658,764, which is a division of application No. 11/811,876, filed on Jun. 12, 2007, now Pat. No. 8,110,658.

(60) Provisional application No. 60/813,284, filed on Jun. 13, 2006.

(51) Int. Cl.
| | |
|---|---|
| *C07K 5/10* | (2006.01) |
| *C07K 5/117* | (2006.01) |
| *C07K 5/103* | (2006.01) |
| *A61K 8/64* | (2006.01) |
| *A61Q 19/00* | (2006.01) |
| *C07K 14/78* | (2006.01) |
| *A61K 38/00* | (2006.01) |

(52) U.S. Cl.
CPC .............. *C07K 5/1024* (2013.01); *A61K 8/64* (2013.01); *A61Q 19/00* (2013.01); *C07K 5/1002* (2013.01); *C07K 5/1008* (2013.01); *C07K 14/78* (2013.01); *A61K 38/00* (2013.01)

(58) Field of Classification Search
CPC ............................... C07K 5/1024; C07K 5/10
USPC ........................................................ 530/330
See application file for complete search history.

(56) References Cited

U.S. PATENT DOCUMENTS

2006/0159659 A1    7/2006    Hallenbeck et al.

FOREIGN PATENT DOCUMENTS

| EP | 0858808 A | 8/1998 |
|---|---|---|
| EP | 1074620 A1 | 2/2001 |
| WO | 2005048968 A1 | 6/2005 |

OTHER PUBLICATIONS

Chemical Abstracts Accession, vol. 88, 1978; pp. 687-688.
Patent Examination Report No. 1 from the Australian Patent Office for related Australian Patent Application No. 2012216555 dated Jun. 12, 2013.
European Search Report and Search Opinion dated Mar. 22, 2012, issued in European Patent Application No. 11175264.8.
Gautier, Moroy et al., "Structrual Characterization of Human Elastin Derived Peptides Containing the GXXP Sequence", Biopolymers, Jul. 1, 2005, pp. 206-220, XP55022638.
Umezawa, Yukiko et al., Novel Proyl Tri/Tetra-Peptidyl Aminopeptidase from Streptomyces Mobaresnsis: Substrate Specificity and Enzyme Gene Cloning:, Journal of Biochemistry (Tokyo), Sep. 2004, pp. 293-300 vol. 136, No. 3, XP002672088.
Hollosi, M. et al., "Studies on Proline-Containing Tetrapeptide Models of (beta)-turns", Biopolymers, Jan. 1, 1985. pp. 211-242, vol. 24, No. 1, XP55022642.
Odake et al., "Vertebrate Collagenase Inhibitor II. Tetrapeptidyl Hydroxamic Acids", Jan. 1, 1991, pp. 1489-1494, vol. 39, No. 6, XP002155190.
European Search Report and Search Opinion dated Nov. 29, 2011, issued in Eruopean Patent Application 11175263.
Katayama, E A K: "A Pentapeptide from Type I Procollagen Promotes Extracellular Matrix Production", Journal of Biological Chemistry, American Society of Biolochemical Biologists, Birmingham, US, vol. 268, No. 14, May 15, 1993, pp. 9941-9944.
Kessler E, et al., A Novel Amino Peptidase from Clostridium-Histolyticum:, Biochemical and Biophysical Research Communications, vol. 50, No. 2, 1973, pp. 405-412.
Heyns, K., et al, "Die Synthese von Tri-und Tetrapeptidderivaten des Prolins und Hydroxyprolins", Hoppe-Seyler's Zeitschrift Fuer Physiologische Chemie, Walter De Gruyter, Berlin, DE, vol. 321, Dec. 2, 1960, pp. 161-183.
Improta, R., et al., "Understanding the Role of Steroelectronic Effects in Determining Collagen Stability. 2. A Quantum Mechanical Molecular Mechanical Study of (Proline-Proline-Glycine) Polypeptides", J. AM. Chem Soc., vol. 124, No. 26, published Jun. 7, 2002.
Morgan, K, et al., "Identification of an immunodominant B-cell epitope in bovine type II collagen and the production of antibodies to type II collagen by immunization with a synthetic peptide representing this epitope", Immunology, published Jul. 8, 1992; vol. 77, pp. 609-616.
Wunsch, Erich, et al., "Zur Spezifitat der Kollagenase" Hoppe-Seyler Z. Physiol. Chem., Bd. 352, S. 1568-1579, Nov. 1971.
Degryse, Bernard, et al., "Domain 2 of the Urokinase Receptor Contains an Integrin-interacting Epitope with Intrinsic Signaling Activity"; The Journal of Biological Chemistry, vol. 280, No. 26, Issue of Jul. 1, pp. 24792-24803, 2005.

*Primary Examiner* — David Lukton
(74) *Attorney, Agent, or Firm* — Thomson Law PLLC

(57) ABSTRACT

Short biologically active tetrapeptides are disclosed that are comprised of the sequences GxxG and PxxP where G (glycine) and P (proline) are maintained and x is a variable amino acid. The peptides can be used singly or in combination to stimulate production of extracellular matrix proteins in skin. A rapid, low-cost method of producing heterogenous formulations of tetrapeptides is disclosed.

9 Claims, 3 Drawing Sheets

```
MGPRLSVWLL LLPAALLLHE EHSRAAAKGG CAGSGCGKCD CHGVKGQKGE
RGLPGLQGVI GFPGMQGPEG PQGPPGQKGD TGEPGLPGTK GTRGPPGASG
YPGNPGLPGI PGQDGPPGPP GIPGCNGTKG ERGPLGPPGL PGFAGNPGPP
GLPGMKGDPG EILGHVPGML LKGERGFPGI PGTPGPPGLP GLQGPVGPPG
FTGPPGPPGP PGPPGEKGQM GLSFQGPKGD KGDQGVSGPP GVPGQAQVQE
KGDFATKGEK GQKGEPGFQG MPGVGEKGEP GKPGPRGKPG KDGDKGEKGS
PGFPGEPGYP GLIGRQGPQG EKGEAGPPGP PGIVIGTGPL GEKGERGYPG
TPGPRGEPGP KGFPGLPGQP GPPGLPVPGQ AGAPGFPGER GEKGDRGFPG
TSLPGPSGRD GLPGPPGSPG PPGQPGYTNG IVECQPGPPG DQGPPGIPGQ
PGFIGEIGEK GQKGESCLIC DIDGYRGPPG PQGPPGEIGF PGQPGAKGDR
GLPGRDGVAG VPGPQGTPGL IGQPGAKGEP GEFYFDLRLK GDKGDPGFPG
QPGMPGRAGS PGRDGHPGLP GPKGSPGSVG LKGERGPPGG VGFPGSRGDT
GPPGPPGYGP AGPIGDKGQA GFPGGPGSPG LPGPKGEPGK IVPLPGPPGA
EGLPGSPGFP GPQGDRGFPG TPGRPGLPGE KGAVGQPGIG FPGPPGPKGV
DGLPGDMGPP GTPGRPGFNG LPGNPGVQGQ KGEPGVGLPG LKGLPGLPGI
PGTPGEKGSI GVPGVPGEHG AIGPPGLQGI RGEPGPPGLP GSVGSPGVPG
IGPPGARGPP GGQGPPGLSG PPGIKGEKGF PGFPGLDMPG PKGDKGAQGL
PGITGQSGLP GLPGQGAPG IPGFPGSKGE MGVMGTPGQP GSPGPVGAPG
LPGEKGDHGF PGSSGPRGDP GLKGDKGDVG LPGKPGSMDK VDMGSMKGQK
GDQGEKGQIG PIGEKGSRGD PGTPGVPGKD GQAGQPGQPG PKGDPGISGT
PGAPGLPGPK GSVGGMGLPG TPGEKGVPGI PGPQGSPGLP GDKGAKGEKG
QAGPPGIGIP GLRGEKGDQG IAGFPGSPGE KGEKGSIGIP GMPGSPGLKG
SPGSVGYPGS PGLPGEKGDK GLPGLDGIPG VKGEAGLPGT PGPTGPAGQK
GEPGSDGIPG SAGEKGEPGL PGRGFPGFPG AKGDKGSKGE VGFPGLAGSP
GIPGSKGEQG FMGPPGPQGQ PGLPGSPGHA TEGPKGDRGP QGQPGLPGLP
GPMGPPGLPG IDGVKGDKGN PGWPGAPGVP GPKGDPGFQG MPGIGGSPGI
TGSKGDMGPP GVPGFQGPKG LPGLQGIKGD QGDQGVPGAK GLPGPPGPPG
PYDIIKGEPG LPGPEGPPGL KGLQGLPGPK GQQGVTGLVG IPGPPGIPGF
DGAPGQKGEM GPAGPTGPRG FPGPPGPDGL PGSMGPPGTP SVDHGFLVTR
HSQTIDDPQC PSGTKILYHG YSLLYVQGNE RAHGQDLGTA GSCLRKFSTM
PFLFCNINNV CNFASRNDYS YWLSTPEPMP MSMAPITGEN IRPFISRCAV
CEAPAMVMAV HSQTIQIPPC PSGWSSLWIG YSFVMHTSAG AEGSGQALAS
PGSCLEEFRS APFIECHGRG TCNYYANAYS FWLATIERSE MFKKPTPSTL
KAGELRTHVS RCQVCMRRT
```

FIG. 1

```
MMSFVQKGSW LLLALLHPTI ILAQQEAVEG GCSHLGQSYA DRDVWKPEPC
QICVCDSGSV LCDDIICDDQ ELDCPNPEIP FGECCAVCPQ PPTAPTRPPN
GQGPQGPKGD PGPPGIPGRN GDPGIPGQPG SPGSPGPPGI CESCPTGPQN
YSPQYDSYDV KSGVAVGGLA GYPGPAGPPG PPGPPGTSGH PGSPGSPGYQ
GPPGEPGQAG PSGPPGPPGA IGPSGPAGKD GESGRPGRPG ERGLPGPPGI
KGPAGIPGFP GMKGHRGFDG RNGEKGETGA PGLKGENGLP GENGAPGPMG
PRGAPGERGR PGLPGAAGAR GNDGARGSDG QPGPPGPPGT AGFPGSPGAK
GEVGPAGSPG SNGAPGQRGE PGPQGHAGAQ GPPGPPGING SPGGKGEMGP
AGIPGAPGLM GARGPPGPAG ANGAPGLRGG AGEPGKNGAK GEPGPRGERG
EAGIPGVPGA KGEDGKDGSP GEPGANGLPG AAGERGAPGF RGPAGPNGIP
GEKGPAGERG APGPAGPRGA AGEPGRDGVP GGPGMRGMPG SPGGPGSDGK
PGPPGSQGES GRPGPPGPSG PRGQPGVMGF PGPKGNDGAP GKNGERGGPG
GPGPQGPPGK NGETGPQGPP GPTGPGGDKG DTGPPGPQGL QGLPGTGGPP
GENGKPGEPG PKGDAGAPGA PGGKGDAGAP GERGPPGLAG APGLRGGAGP
PGPEGGKGAA GPPGPPGAAG TPGLQGMPGE RGGLGSPGPK GDKGEPGGPG
ADGVPGKDGP RGPTGPIGPP GPAGQPGDKG EGGAPGLPGI AGPRGSPGER
GETGPPGPAG FPGAPGQNGE PGGKGERGAP GEKGEGGPPG VAGPPGGSGP
AGPPGPQGVK GERGSPGGPG AAGFPGARGL PGPPGSNGNP GPPGPSGSPG
KDGPPGPAGN TGAPGSPGVS GPKGDAGQPG EKGSPGAQGP PGAPGPLGIA
GITGARGLAG PPGMPGPRGS PGPQGVKGES GKPGANGLSG ERGPPGPQGL
PGLAGTAGEP GRDGNPGSDG LPGRDGSPGG KGDRGENGSP GAPGAPGHPG
PPGPVGPAGK SGDRGESGPA GPAGAPGPAG SRGAPGPQGP RGDKGETGER
GAAGIKGHRG FPGNPGAPGS PGPAGQQGAI GSPGPAGPRG PVGPSGPPGK
DGTSGHPGPI GPPGPRGNRG ERGSEGSPGH PGQPGPPGPP GAPGPCCGGV
GAAAIAGIGG EKAGGFAPYY GDEPMDFKIN TDEIMTSLKS VNGQIESLIS
PDGSRKNPAR NCRDLKFCHP ELKSGEYWVD PNQGCKLDAI KVFCNMETGE
TCISANPLNV PRKHWWTDSS AEKKHVWFGE SMDGGFQFSY GNPELPEDVL
DVQLAFLRLL SSRASQNITY HCKNSIAYMD QASGNVKKAL KLMGSNEGEF
KAEGNSKFTY TVLEDGCTKH TGEWSKTVFE YRTRKAVRLP IVDIAPYDIG
GPDQEFGVDV GPVCFL
```

FIG. 2

```
MGPRLSVWLL  LLPAALLLHE  EHSRAAAKGG  CAGSGCGKCD  CHGVKGQKGE
RGLPGLQGVI  GFPGMQGPEG  PQGPPGQKGD  TGEPGLPGTK  GTRGPPGASG
YPGNPGLPGI  PGQDGPPGPP  GIPGCNGTKG  ERGPLGPPGL  PGFAGNPGPP
GLPGMKGDPG  EILGHVPGML  LKGERGFPGI  PGTPGPPGLP  GLQGPVGPPG
FTGPPGPPGP  PGPPGEKGQM  GLSFQGPKGD  KGDQGVSGPP  GVPGQAQVQE
KGDFATKGEK  GQKGEPGFQG  MPGVGEKGEP  GKPGPRGKPG  KDGDKGEKGS
PGFPGEPGYP  GLIGRQGPQG  EKGEAGPPGP  PGIVIGTGPL  GEKGERGYPG
TPGPRGEPGP  KGFPGLPGQP  GPPGLPVPGQ  AGAPGFPGER  GEKGDRGFPG
TSLPGPSGRD  GLPGPPGSPG  PPGQPGYTNG  IVECQPGPPG  DQGPPGIPGQ
PGFIGEIGEK  GQKGESCLIC  DIDGYRGPPG  PQGPPGEIGF  PGQPGAKGDR
GLPGRDGVAG  VPGPQGTPGL  IGQPGAKGEP  GEFYFDLRLK  GDKGDPGFPG
QPGMPGRAGS  PGRDGHPGLP  GPKGSPGSVG  LKGERGPPGG  VGFPGSRGDT
GPPGPPGYGP  AGPIGDKGQA  GFPGGPGSPG  LPGPKGEPGK  IVPLPGPPGA
EGLPGSPGFP  GPQGDRGFPG  TPGRPGLPGE  KGAVGQPGIG  FPGPPGPKGV
DGLPGDMGPP  GTPGRPGFNG  LPGNPGVQGQ  KGEPGVGLPG  LKGLPGLPGI
PGTPGEKGSI  GVPGVPGEHG  AIGPPGLQGI  RGEPGPPGLP  GSVGSPGVPG
IGPPGARGPP  GGQGPPGLSG  PPGIKGEKGF  PGFPGLDMPG  PKGDKGAQGL
PGITGQSGLP  GLPGQQGAPG  IPGFPGSKGE  MGVMGTPGQP  GSPGPVGAPG
LPGEKGDHGF  PGSSGPRGDP  GLKGDKGDVG  LPGKPGSMDK  VDMGSMKGQK
GDQGEKGQIG  PIGEKGSRGD  PGTPGVPGKD  GQAGQPGQPG  PKGDPGISGT
PGAPGLPGPK  GSVGGMGLPG  TPGEKGVPGI  PGPQGSPGLP  GDKGAKGEKG
QAGPPGIGIP  GLRGEKGDQG  IAGFPGSPGE  KGEKGSIGIP  GMPGSPGLKG
SPGSVGYPGS  PGLPGEKGDK  GLPGLDGIPG  VKGEAGLPGT  PGPTGPAGQK
GEPGSDGIPG  SAGEKGEPGL  PGRGFPGFPG  AKGDKGSKGE  VGFPGLAGSP
GIPGSKGEQG  FMGPPGPQGQ  PGLPGSPGHA  TEGPKGDRGP  QGQPGLPGLP
GPMGPPGLPG  IDGVKGDKGN  PGWPGAPGVP  GPKGDPGFQG  MPGIGGSPGI
TGSKGDMGPP  GVPGFQGPKG  LPGLQGIKGD  QGDQGVPGAK  GLPGPPGPPG
PYDIIKGEPG  LPGPEGPPGL  KGLQGLPGPK  GQQGVTGLVG  IPGPPGIPGF
DGAPGQKGEM  GPAGPTGPRG  FPGPPGPDGL  PGSMGPPGTP  SVDHGFLVTR
HSQTIDDPQC  PSGTKILYHG  YSLLYVQGNE  RAHGQDLGTA  GSCLRKFSTM
PFLFCNINNV  CNFASRNDYS  YWLSTPEPMP  MSMAPITGEN  IRPFISRCAV
CEAPAMVMAV  HSQTIQIPPC  PSGWSSLWIG  YSFVMHTSAG  AEGSGQALAS
PGSCLEEFRS  APFIECHGRG  TCNYYANAYS  FWLATIERSE  MFKKPTPSTL
KAGELRTHVS  RCQVCMRRT
```

FIG. 3

PEPTIDE FRAGMENTS FOR INDUCING SYNTHESIS OF EXTRACELLULAR MATRIX PROTEINS

This application is a continuation of co-pending application SN 13/961,782 filed Aug. 7, 2013, which is continuation of co-pending application SN 13/339,606 filed Dec. 29, 2011, which is a continuation of SN 11/811,876 filed Jun. 12, 2007, which claims benefit of priority to U.S. 60/813,284 filed Jun. 13, 2006, each of which is herein incorporated by reference in its entirety.

FIELD OF THE INVENTION

The invention relates to tetrapeptides with the amino acid motif GxxG or PxxP, where G (glycine) and P (proline) are maintained and x is a variable amino acid. The invention also relates to frame shift active tetrapeptides which are tetrapeptide sequences shifted one frame from a GxxG or PxxP tetrapeptide in an ECM protein. In particular, the invention relates to GxxG, PxxP, or frame shift active peptides that stimulate production of extracellular matrix proteins and enhance wound closure of the epithelial cell monolayer of scratch-wounded human skin. The peptide compositions may be used in formulations for repairing damaged skin or maintaining healthy skin.

BACKGROUND OF THE INVENTION

Skin aging is commonly viewed as wrinkle formation and impaired wound healing. A wound is defined as a break in the epithelial integrity of the skin. Normal wound healing involves a complex and dynamic but superbly orchestrated series of events leading to the repair of injured tissues. The largest component of normal skin is the extracellular matrix (ECM), a gel-like matrix produced by the cells that it surrounds. The ECM is composed of two major classes including fibrous structural proteins and proteoglycans. Changes in the composition and crosslinked state of the ECM are known to be associated with aging and a range of acquired and heritable skin disorders. It has been well documented that ECM not only provides structural support, but also influences cellular behavior such as differentiation and proliferation. Also, more and more research suggests that the matrix components may be a source of cell signals to facilitate epithelial cell proliferation and migration and thus enhance wound healing.

The largest class of fibrous ECM molecules is the collagen family, which includes at least 16 different types of collagen. Collagen in the dermal matrix is composed primarily of type I (80-85%) and type III (8-11%) collagens, both of which are fibrillar, or rod-shaped, collagens. The tensile strength of skin is due predominately to these fibrillar collagen molecules, which self-assemble into microfibrils in a head-to-tail and staggered side-to-side lateral arrangement. Collagen molecules become cross-linked to adjacent collagen molecules, creating additional strength and stability in collagen fibers. Damage to the collagen network (e.g. by enzymes or physical destruction), or its total collapse causes healing to take place by repair.

Various bioactive peptides that stimulate production of ECM proteins have been reported in both the scientific literature and in issued patents. Peptides historically have been isolated from natural sources and have recently been the subject of structure-function relationship studies. Natural peptides have also served as starting points for the design of synthetic peptide analogs.

Specific sequences within ECM proteins can stimulate useful elements in skin, such as type I collagen, type III collagen, and fibronectin (Katayama et. al., J. BIOL. CHEM. 288:9941-9944 (1983)). Katayama et al. identified the pentapeptide, KTTKS (SEQ ID NO: 17), within the carboxy-terminal propeptide (residues 197-241) of type I collagen. The propeptide is cleaved during production of the mature collagen protein. The cleaved propeptide may participate in regulating collagen production via a biosynthesis feedback mechanism, with the KTTKS segment playing an active role. Maquart et al. (J Soc BIOL. 193:423-28 (1999)) reported that the peptides GHK and CNYYSNS also stimulate ECM synthesis. These sequences may be released during ECM turnover, thereby signaling the need for ECM repair. The short peptide sequences liberated by either mechanism are often called "matrikines" (Maquart et al., J. Soc. BIOL. 193:423-28 (1999)).

While a number of natural and synthetic peptides exist, there is a need for improved biologically active peptides and methods for their use.

SUMMARY OF THE INVENTION

Tetrapeptides are disclosed that are characterized by the amino acid sequence motif GxxG or PxxP, where G (glycine) and P (proline) residues are maintained and x is a variable amino acid. The tetrapeptides are derived from sequences that occur multiple times throughout the primary sequence of the ECM protein, type IV collagen. The disclosed sequences induce production of all forms of collagen more than previously known peptide sequences, including KTTKS, sold under the trademark MATRIXYL™ by SEDERMA SAS (France). Further, a composition comprising a combination of various multiply-repeating sequences elicits an even greater collagen-producing response. Additional benefits may be expected from peptide combinations present in a variety of ECM proteins.

Producing a specific combination of tetrapeptides for ECM rebuilding can be commercially cost-prohibitive. A relatively simple and cost-effective means of producing a diverse combination of biologically active tetrapeptides is disclosed. By producing a combinatorial library of tetrapeptides with the GxxG or PxxP motif, a variety of biologically active tetrapeptides can be generated in the same manufacturing run (e.g., GEPG, GPEG, GPPG, and GEEG). The combination of tetrapeptides may induce more formation of ECM proteins than single peptides. Compositions comprising the disclosed tetrapepides, alone or in combination, are useful in skin care markets including, but not limited to, those that address skin wrinkling, toning, firmness, or sagging. The stimulation of collagen by the disclosed tetrapeptides can significantly improve the health and appearance of damaged and aged skin.

BRIEF DESCRIPTION OF THE FIGURES

FIG. 1 is SEQ ID NO: 45 which is the Collagen IV amino acid sequence illustrating the occurrences of GxxG tetrapeptides. All bold sequences are underlined and overlapping sequences are double-underlined.

FIG. 2 is SEQ ID NO: 46 which is the Collagen III amino acid sequence illustrating the occurrences of the frame shift actives PGPR and GAGP. All frame shift active sequences are bold and underlined and the GxxG sequences occurring one frame shift away are double-underlined.

FIG. 3 is also SEQ ID NO: 45, the Collagen IV amino acid sequence, illustrating the occurrences of the tetrapeptide PGPP.

DETAILED DESCRIPTION OF THE INVENTION

The invention is generally directed towards tetrapeptides that stimulate production of ECM proteins and modulate wound healing, and uses of such tetrapeptides.

Peptides

One embodiment of the invention is directed towards an isolated tetrapeptide comprising the motif GxxG or PxxP. In this embodiment G (glycine) or P (proline) is maintained and x is a variable amino acid. The peptide can generally be any peptide that falls within the above description, and more preferably is SEQ ID NO: 1, SEQ ID NO: 2, SEQ ID NO: 3, SEQ ID NO: 5, SEQ ID NO: 7, SEQ ID NO: 8, SEQ ID NO: 9, SEQ ID NO: 10, SEQ ID NO: 11, SEQ ID NO: 12. SEQ ID NO: 13, SEQ ID NO: 14, SEQ ID NO: 15, or SEQ ID NO: 16.

Another embodiment of the invention is directed towards an isolated tetrapeptide comprising the motif GxPG, where x is P at either variable position, or both. In this embodiment, G (glycine) and P (proline) are maintained and x is a variable amino acid. The peptide can generally be any peptide that falls within the above description, and more preferably is SEQ ID NO: 2, SEQ ID NO: 3, SEQ ID NO: 5, or SEQ ID NO: 7.

Another embodiment of the invention is directed towards an isolated tetrapeptide comprising the motif GExG. In this embodiment, G (glycine) and E (glutamic acid) are maintained and x is a variable amino acid. The peptide can generally be any peptide that falls within the above description, and more preferably is SEQ ID NO: 5 or SEQ ID NO: 8.

Another embodiment of the invention is directed towards an isolated tetrapeptide comprising the motif PGxP. In this embodiment, P (proline) and G (glycine) are maintained and x is a variable amino acid. The peptide can generally be any peptide that falls within the above description, and more preferably is SEQ ID NO: 11, SEQ ID NO: 12, SEQ ID NO: 14, or SEQ ID NO: 16.

Another embodiment of the invention is directed towards an isolated tetrapeptide comprising the motif PExP. In this embodiment, P (proline) and E (glutamic acid) are maintained and x is a variable amino acid. The peptide can generally be any peptide that falls within the above description, and more preferably is SEQ ID NO: 1 or SEQ ID NO: 9.

Another embodiment of the invention is directed towards a frame shift active tetrapeptide. In this embodiment, the tetrapeptide occurs one frame shift from either a GxxG or PxxP tetrapeptide in an ECM protein. The peptide can generally be any peptide that falls within the above description, and more preferably is SEQ ID NO: 4 or SEQ ID NO: 6.

Each of the above-described peptides can comprise D- or L-amino acids. The peptides can comprise all D-amino acids or L-amino acids. The peptides can have an acid C-terminus (—CO$_2$H) or, preferably, an amide C-terminus (—CONH$_2$, —CONHR, or —CONR$_2$). The peptides may be further augmented or modified, either chemically or enzymatically. For example, the peptides may be amidated (—NH$_2$) on the C-terminus, which may render the tetrapeptide less susceptible to protease degradation and increase their solubility compared to the free acid forms. The peptides may also be lipidated which may provide for enhanced skin penetration.

The above-described peptides may contain the following amino acids: R (arginine), L (leucine), P (proline), F (phenylalanine), Q (glutamine), E (glutamic acid), I (isoleucine), K (lysine), S (serine), V (valine), A (alanine), N (asparagine), D (aspartic acid), T (threonine), Y (tyrosine) and G (glycine). The above-described peptides do not include the following M (methionine), C (cysteine), H (histidine) or W (tryptophan). Accordingly, in one embodiment, x is not selected from either (methionine), C (cysteine), H (histidine) or W (tryptophan).

Methods of Use

An additional embodiment of the invention is directed towards methods of using the above-described peptides. The methods of use may involve the use of a single peptide, or may involve the use of two or more peptides in combination.

An embodiment of the invention is a method of promoting repair of damaged skin and maintenance of healthy skin using tetrapeptides that stimulate production of ECM proteins. The method generally is directed towards contacting dermal (skin) cells with a composition containing the peptide. The compositions can be an aerosol, emulsion, liquid, lotion, cream, paste, ointment, foam, or other pharmaceutically acceptable formulation. Generally, a pharmaceutically acceptable formulation would include any acceptable carrier suitable for use on human skin, e.g. cosmetically acceptable carrier and dermatological acceptable carrier. The compositions may contain other biologically active agents such as retinoids or other peptides. The compositions may contain pharmaceutically acceptable carriers or adjuvants. The contacting step can be performed in vivo, in situ, in vitro, or by any method known to those of skill in the art. Most preferably, the contacting step is to be performed topically at a concentration sufficient to elicit a stimulatory response. The concentration of the peptide in the composition can be about 0.01 µg/mL to about 100 µg/mL, about 0.1 µg/mL to about 50 µg/mL, and about 0.1 µg/mL to about 1 µg/mL. The contacting step can be performed on a mammal, a cat, a dog, a cow, a horse, a pig, or a human. A preferred composition for promoting ECM protein production comprises SEQ ID NO: 8; more preferably, the composition comprises SEQ ID NO: 8 in a heterogeneous mixture with at least one other tetrapeptide. In a most preferred embodiment, the individual tetrapeptides in the composition would cause sustained collagen production over a period of at least 48 hours.

An additional embodiment of the invention is directed towards a method for promoting wound healing of skin damaged by normal aging, disease, injury, trauma, or by surgery or other medical procedures. The method can comprise administering to the wound of an animal a composition, wherein the composition comprises any of the above-described peptides, singularly or in combination. The compositions can be a liquid, lotion, cream, paste, ointment, foam, or any other pharmaceutically acceptable formulation. The compositions may contain pharmaceutically acceptable carriers or adjuvants. The compositions may contain other biologically active agents such as antimicrobial agents or growth factors. The compositions may also be used in combination with other therapeutic agents such as tissue grafts, tissue culture products, oxygen or dressings. The concentration of the peptide in the composition can be about 0.01 µg/mL to about 100 µg/mL, about 0.1 µg/mL to about 50 µg/mL, and about 0.1 µg/mL to about 1 µg/mL. The composition can be administered to the wound topically. The animal can generally be any kind of animal, and preferably is a mammal, and more preferably is a human, cow, horse, cat, dog, pig, goat, or sheep. A preferred composition for wound healing applications in which ECM protein production is promoted comprises SEQ ID NO: 8; more preferably, the composition comprises SEQ ID NO: 8 in a heterogeneous mixture with at least one other tetrapeptide. In a most preferred embodiment, the individual tetrapeptides in the composition would cause sustained collagen production over a period of at least 48 hours.

An additional embodiment of the invention is directed towards a method for reducing scarring of skin damaged by normal aging, disease, injury, trauma, or by surgery or other medical procedures. The method can comprise administering to the wound of an animal a composition, wherein the composition comprises any of the above-described peptides, singularly or in combination. The compositions can be a liquid, lotion, cream, paste, ointment, foam, or other pharmaceutically acceptable formulation. The compositions may contain pharmaceutically acceptable carriers or adjuvants. The compositions may contain other biologically active agents such as antimicrobial agents or growth factors. The compositions may also be used in combination with other therapeutic agents such as tissue grafts, tissue culture products, oxygen or dressings. The concentration of the peptide in the composition can be about 0.01 µg/mL to about 100 µg/mL, about 0.1 µg/mL to about 50 µg/mL, and about 0.1 µg/mL to about 1 µg/mL. The composition can be administered to the wound topically. The animal can generally be any kind of animal, and preferably is a mammal, and more preferably is a human, cow, horse, cat, dog, pig, goat, or sheep. A preferred composition for wound healing applications in which ECM protein production is promoted comprises SEQ ID NO: 8; more preferably, the composition comprises SEQ ID NO: 8 in a heterogeneous mixture with at least one other tetrapeptide. In a most preferred embodiment, the individual tetrapeptides in the composition would cause sustained collagen production over a period of at least 48 hours.

A further embodiment of the invention is directed towards a method for producing the disclosed tetrapeptides in combination. The peptides may be produced using any method known to those skilled in the art such as those disclosed in Merrifield, R. B., *Solid Phase Peptide Synthesis I.*, J. AM. CHEM. SOC. 85:2149-2154 (1963); Carpino, L.A. et al., [(9-*Fluorenylmethyl*) *Oxy*] *Carbonyl* (*Fmoc*) *Amino Acid Chlorides: Synthesis, Characterization, And Application To The Rapid Synthesis Of Short Peptides*, J. ORG. CHEM. 37:51: 3732-3734; Merrifield, R. B. et al., *Instrument For Automated Synthesis Of Peptides*, ANAL. CHEM. 38:1905-1914 (1966); or Kent, S. B. H. et al., *High Yield Chemical Synthesis Of Biologically Active Peptides On An Automated Peptide Synthesizer Of Novel Design*, IN: PEPTIDES 1984 (Ragnarsson U., ed.) Almqvist and Wiksell Int., Stockholm (Sweden), pp. 185-188, all of which are incorporated by reference herein in their entirety. Preferably, the peptides will be produced by a machine capable of sequential addition of amino acids to a growing peptide chain. However, the peptides may also be manufactured using standard solution phase methodology.

It has been observed that the addition of a mixture of free amino acids instead of homogenous peptide mixtures during peptide chain synthesis results in varied incorporation of free amino acids such that a combination of peptides results from the synthesis reactions. The relative incorporation frequency of a particular amino acid included in a mixture of two or more amino acids added during synthesis may be adjusted. Adjustment is made possible by modifying the ratio of a free amino acid made available during the synthesis process relative to the other amino acids in the mixture (this is termed an isokinetic mixture).

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Identification of Repeat Tetrapeptide Sequences in Collagen

A relatively high proportion of collagen IV tetrapeptide repeat sequences have the motif GxxG (where x is any amino acid). A number of these are shown in situ as part of the full collagen IV sequence illustrated in FIG. 1 as SEQ ID NO: 45. Collagen IV was examined first due to its role of interacting with other specialized ECM components (See Gregory Schultz et al., 2005). There are eleven sequences with the GxxG motif in collagen IV that appear more than ten times (GxxG where xx is represented by: vp, ek, fp, 1p, pp, sp, ep, ip, pk, qp and tp). Of these tetrapeptide sequences, eight of eleven sequences contain proline in position 3, two of eleven sequences contain P in position 2, one of eleven sequences contains proline in positions 2 and 3, and one of eleven sequences contains no proline. The disclosed sequences are referred to as REPLIKINES™. "REPLIKINE" is defined as a short sequence within ECM proteins that occurs multiple times (i.e., is replicated). This sequence may be present in one ECM protein (e.g., collagen IV). Preferably, the sequence is present in multiple ECM proteins (e.g., all collagens, elastin, laminin, etc.). The presence of the sequence in multiple ECM proteins increases the likelihood that the fragment may be able to promote ECM synthesis or repair.

The eleven GxxG sequences appearing in collagen IV listed above are highlighted in the human collagen IV sequence illustrated in FIG. 1. In this figure, all bold sequences are underlined and overlapping sequences are double-underlined. All but one of these sequences also appears in collagens I, II, III, and V. This fact contributes to the ability of the disclosed peptides to stimulate the production of all collagen types, particularly when the peptides are used in combination. Table 1 shows the frequency of several tetrapeptide repeats in ECM proteins. Bold sequences in Table 1 are those that appear in collagen IV ten or more times.

TABLE 1

Frequency of tetrapeptides in ECM proteins

| SEQ. ID NO | Sequence | Collagen I | Collagen II | Collagen III | Collagen IV | Collagen V | Elastin | Elastin Precursor |
|---|---|---|---|---|---|---|---|---|
| 19 | GAAG | 10 | 5 | 7 | | 2 | 4 | 5 |
| 20 | GAKG | 3 | 4 | 3 | 5 | 5 | | |
| 21 | GAPG | 13 | 21 | 25 | 6 | 9 | | |
| 22 | GDKG | 2 | 2 | 4 | 9 | 3 | | |
| 23 | GDRG | 2 | 5 | 2 | 4 | 1 | | |
| 8 | GEKG | 3 | 5 | 4 | 22 | 15 | | |
| 5 | GEPG | 11 | 15 | 10 | 11 | 4 | | |
| 24 | GERG | 10 | 11 | 14 | 6 | 7 | | |
| 2 | GFPG | 4 | 8 | 6 | 22 | 5 | 1 | 1 |
| 25 | GIPG | 2 | 2 | 6 | 14 | 6 | 5 | 5 |
| 26 | GKDG | 1 | 4 | 5 | 2 | 2 | | |
| 27 | GKPG | 2 | 3 | 3 | 4 | 1 | | |
| 28 | GLKG | 2 | 1 | 1 | 5 | 4 | | |
| 29 | GLPG | 15 | 10 | 9 | 42 | 15 | 1 | 1 |
| 30 | GNPG | 3 | 5 | 3 | 2 | 1 | | |
| 31 | GPAG | 16 | 20 | 20 | 3 | 6 | | |
| 32 | GPKG | 3 | 11 | 4 | 12 | 9 | | |
| 7 | GPPG | 33 | 40 | 40 | 46 | 43 | | |
| 33 | GPQG | 7 | 11 | 9 | 7 | 5 | | |
| 34 | GPRG | 11 | 13 | 10 | 4 | 7 | | |
| 35 | GPSG | 10 | 11 | 5 | 1 | 5 | | |
| 36 | GPTG | 4 | 3 | 2 | 2 | 6 | | |
| 37 | GPVG | 9 | 3 | 3 | 2 | 5 | | |
| 38 | GQPG | 3 | 4 | 6 | 12 | 7 | | |
| 39 | GRDG | 4 | 2 | 3 | 3 | | | |
| 40 | GRPG | 3 | 3 | 4 | 2 | 5 | | |
| 3 | GSPG | 4 | 6 | 21 | 16 | 3 | | |
| 41 | GTPG | 3 | 4 | 2 | 11 | 2 | | |
| 42 | GVKG | 1 | 3 | 2 | 3 | 1 | | |
| 43 | GVPG | | 1 | 3 | 10 | 1 | 14 | 15 |
| 44 | GYPG | 1 | 1 | 1 | 4 | 2 | | |

As also evident from a review of the collagen IV sequence, SEQ ID NO: 45, there are also many occurrences of sequences having the PxxP motif. For example, the sequence PGPP occurs no less than fifteen times as illustrated in FIG. 3. Therefore, this disclosed sequence is also referred to as a REPLIKINE™. Preferably, this sequence is present in multiple ECM proteins (e.g., all collagens, elastin, laminin, etc.) as the presence of this sequence in multiple ECM proteins increases the likelihood that the fragment may be able to promote ECM synthesis or repair. The fifteen PGPP sequences appearing in collagen IV listed above are highlighted and underlined in the human collagen IV sequence illustrated in FIG. 3.

Example 2

Identification of Frame Shift Actives

In addition to the relatively high proportion of collagen IV tetrapeptide repeat sequences with the motif GxxG, other tetrapeptide sequences occurring one amino acid frame shift away from a GxxG or PxxP tetrapeptide sequence have been identified. These sequences may repeat or occur only once within an ECM protein and may be located one amino acid position away from either a GxxG or PxxP tetrapeptide sequence as described herein. These tetrapeptide sequences are referred to as frame shift actives. Such frame shift actives may accordingly contain either a G or a P in either the second or third position depending on the direction of frame shift. It has been further recognized that frame shift actives may be combined with other tetrapeptide sequences disclosed in this application forming a combikine. An example of such a combikine is H06 and H15.

One example of a frame shift active is GAGP or H12 (SEQ ID NO: 6). H12 (GAGP) appears one residue (or frame) shift from the GxxG tetrapeptide GGAG in Collagen III (SEQ ID NO: 46) as illustrated in FIG. 2. In this figure, all frame shift active sequences are bold and underlined and the GxxG sequences occurring one frame shift away are double-underlined. Furthermore, as shown in Table 5, this tetrapeptide (GAGP) achieves good results for collagen production at 48 hours. Another example is the sequence PGPR, which is H10 (SEQ ID NO: 4) which occurs eleven times in Collagens I-IV. As it appears multiple times in an individual ECM protein, this tetrapeptide would further be considered a REPLIKINE. FIG. 2 (SEQ ID NO: 46) illustrates several instances of this tetrapeptide with each occurring one frame shift from the GxxG tetrapeptide GPRG. This particular frame shift active appears in multiple ECM proteins and therefore increases the likelihood that the fragment may be able to promote ECM synthesis or repair.

Example 3

Identification of Repeat Sequences that Stimulate Collagen Production

Several sequences identified in Examples 1 and 2 were synthesized using standard peptide chemistry and assayed for the stimulation of collagen from dermal fibroblasts. The synthesized peptides were amidated at the C-terminus, which rendered the tetrapeptides less susceptible to protease degradation and increased their solubility compared to the free acid forms. Human dermal fibroblasts were incubated in 96-well plates at 37° C. and 5% $CO_2$ for 24 and 48 hours in 150 µL. complete cell culture media (Cascade Biologics, Portland, Oreg.; Cat. No. M-106-500), supplemented with Low Serum Growth Supplement (Cascade Biologics, Portland, Oreg.; Cat. No. S-003-10) containing sample peptides at a final peptide concentration of 50 µg/mL. Each well was seeded with 10,000 cells. Following the incubation, 100-µL medium samples were recovered from each well and assayed for collagen production The assays were performed by Tebu-bio Laboratories (France) using the SIRCOL™ Collagen Assay Kit (Biocolor Assays, UK) following the manufacturer's protocol. The SIRCOL™ Collagen Assay is a quantitative dye-binding method designed for the analysis of soluble collagens released into culture medium by mammalian cells during in vitro culture. The collagen of the tested samples binds to the anionic SIRCOL™ dye. The collagen-dye complexes precipitate out of solution and are pelleted by centrifugation. The recovered collagen-dye pellet was dissolved in an alkaline solution prior to absorbance measurements. Duplicate measurements were taken at the 24 and 48 hour times from two separate samples. The four measurements for each sample were averaged. The absorbance of reagent blanks, collagen standards, and samples were measured at 560 nm. The reagent blank absorbance was subtracted from the absorbance from each sample at 24 and 48 hours.

Two separate data sets were used to generate two collagen standard calibration curves. The first calibration curve was generated for purposes of calculating the quantity of collagen in samples H6 (combination of SEQ ID NOs:1-4), H7-H14 (SEQ ID NOs:1-8, respectively) and H15 (combination of SEQ ID NOs:5-8). The second calibration curve was generated for calculating the quantity of collagen in samples H16 (SEQ ID NO: 9), H21-23 (SEQ ID NOs:10-12, respectively), H25-26 (SEQ ID NOs:13-14, respectively), or H29-30 (SEQ ID NOs:15-16, respectively), H32 (SEQ ID NO: 17), H33 (combination of SEQ ID NOs:9-12), H34 (combination of SEQ ID NOs:11-14), H35 (combination of SEQ ID NOs:13-16), H36 (combination of SEQ ID NOs:1, 6, 5, 8), H37 (SEQ ID NO: 17) and H38 (SEQ ID NO: 8) from the absorbance measurements was created by plotting the $Abs_{560\ nm}$ of the known collagen standards versus the respective concentrations of the collagen standards (in micrograms) each time a series of assays were performed. With respect to each data set, the same calibration curve was used for samples taken at the 24 and 48 hour times (Tables 2A and 2B). Accordingly, different standard curves were prepared immediately prior to performing each series of assays.

TABLE 2A

| Calibration curve for assaying collagen production by peptides H6-H15 | | |
|---|---|---|
| Collagen standards (µg) | $A_{560\ nm}$ 24 h test | $A_{560\ nm}$ 48 h test |
| 0 | 0.00 | 0.00 |
| 5 | 0.08 | 0.10 |
| 10 | 0.11 | 0.15 |
| 25 | 0.32 | 0.35 |
| 50 | 0.66 | 0.65 |

TABLE 2B

| Calibration curve for assaying collagen production by peptides H16, H21-23, H25-26, and H29-38 | | |
|---|---|---|
| Collagen Standards (µg) | $A_{560\ nm}$ Assay date 1 | $A_{560\ nm}$ Assay date 2 |
| 0 | 0.00 | 0.00 |
| 5 | 0.12 | 0.09 |
| 10 | 0.14 | 0.15 |
| 25 | 0.48 | 0.42 |
| 50 | 0.88 | 0.80 |

A linear regression was performed from plotting the $Abs_{560\ nm}$ values versus concentrations of the respective collagen standards using MICROSOFT EXCEL™. The regression resulted in a lines described by the formula y=0.013x for both incubation times noted in Table 2A. As the results were identical, only the 24-hour time period was used for the second series calibration curves. The formula of the line obtained on assay date 1 and assay date 2 of the second series of samples was y=0.0178x and y=0.0162x, respectively. The peptide LL-37 (SEQ ID NO: 18) was used as a positive control as it has been widely reported to have an impact upon wound healing in man (Heilborn et al., The Cathelicidin Anti-Microbial Peptide LL-37 Is Involved In The Re-Epithelialization Of Human Skin Wounds And Is Lacking In Chronic Ulcer Epithelium, *J. Invest. Dermato.* 120:379-89 (2003)). The assay detection limit defined by the manufacturer is 2.5 μg.

The total amount of collagen produced in samples containing peptides was calculated from the averaged absorbance values taken at 24 hours (Table 3A) and 48 hours (Table 3B) using the linear equation derived from the standard curve. The total amount of collagen produced in samples containing peptides H16 (SEQ ID NO: 9), H21-23 (SEQ ID NOs:10-12, respectively), H25-26 (SEQ ID NOs: 13-14, respectively), or H29-30 (SEQ ID NOs:15-16, respectively), H32 (SEQ ID NO: 17), H33 (combination of SEQ ID NOs:9-12), H34 (combination of SEQ ID NOs:11-14), H35 (combination of SEQ ID NOs:13-16), H36 (combination of SEQ ID NOs:1, 6, 5, 8), H37 (SEQ ID NO: 17) and H38 (SEQ ID NO: 8) was calculated from the absorbance values taken at 24 hours (Table 4A) and 48 hours (Table 4B) using the linear equation derived from the standard curve. These values were compared with peptide LL37 (SEQ ID NO: 18), a peptide known to stimulate collagen. In each table, samples marked by an asterisk (*) may not be significant as the assay detection limit is 2.5 μg.

TABLE 3A

Absorbance measurements and quantification of collagen in test samples H6-H15 at 24 hours.

| SEQ ID NO | Peptides | $A_{560\,nm}$ | | Average | Average minus blank | Collagen (μg) |
|---|---|---|---|---|---|---|
| 18 | LL37 | 0.102 | 0.136 | 0.12 | 0.04 | 3.0 |
| — | H6 | 0.084 | 0.140 | 0.11 | 0.03 | 2.5 |
| 1 | H7 | 0.098 | 0.063 | 0.08 | 0.00 | 0.0* |
| 2 | H8 | 0.122 | 0.078 | 0.10 | 0.02 | 1.5* |
| 3 | H9 | 0.147 | 0.104 | 0.13 | 0.05 | 3.5 |
| 4 | H10 | 0.103 | 0.146 | 0.12 | 0.04 | 3.4 |
| 5 | H11 | 0.110 | 0.168 | 0.14 | 0.06 | 4.5 |
| 6 | H12 | 0.063 | 0.101 | 0.08 | 0.00 | 0.2* |
| 7 | H13 | 0.114 | 0.093 | 0.10 | 0.02 | 1.8* |
| 8 | H14 | 0.115 | 0.122 | 0.12 | 0.04 | 3.0 |
| — | H15 | 0.132 | 0.093 | 0.11 | 0.03 | 2.5 |
| — | Blank | 0.074 | 0.076 | 0.08 | 0.00 | 0.0 |

TABLE 3B

Absorbance measurements and quantification of collagen in test samples H6-H15 at 48 hours.

| SEQ ID NO | Peptides | $A_{560\,nm}$ | | Average | Average minus blank | Collagen (μg) |
|---|---|---|---|---|---|---|
| 18 | LL37 | 0.262 | 0.113 | 0.19 | 0.07 | 5.2 |
| — | H6 | 0.086 | 0.189 | 0.14 | 0.02 | 1.3* |
| 1 | H7 | 0.192 | 0.189 | 0.19 | 0.07 | 5.4 |
| 2 | H8 | 0.137 | 0.126 | 0.13 | 0.01 | 0.9* |
| 3 | H9 | 0.117 | 0.061 | 0.09 | 0.00 | 0.0* |
| 4 | H10 | 0.136 | 0.085 | 0.11 | 0.00 | 0.0* |
| 5 | H11 | 0.113 | 0.181 | 0.15 | 0.03 | 2.1* |
| 6 | H12 | 0.106 | 0.231 | 0.17 | 0.05 | 3.7 |
| 7 | H13 | 0.100 | 0.145 | 0.12 | 0.00 | 0.2* |
| 8 | H14 | 0.132 | 0.176 | 0.15 | 0.03 | 2.6 |
| — | H15 | 0.177 | 0.174 | 0.18 | 0.06 | 4.3 |
| — | Blank | 0.120 | 0.115 | 0.12 | 0.00 | 0.0 |

TABLE 4A

Absorbance measurements and quantification of collagen in test samples H16, H21-23, H25-26, or H29-38 at 24 hours.

| SEQ ID NO | Peptides | $A_{560\,nm}$ | | Average | Average minus blank | Collagen (μg) |
|---|---|---|---|---|---|---|
| 9 | H16 | 0.133 | 0.137 | 0.14 | 0.06 | 3.1 |
| 10 | H21 | 0.129 | 0.119 | 0.12 | 0.04 | 2.5 |
| 11 | H22 | 0.192 | 0.085 | 0.14 | 0.06 | 3.3 |
| 12 | H23 | 0.090 | 0.073 | 0.08 | 0.00 | 0.1* |
| 13 | H25 | 0.129 | 0.076 | 0.10 | 0.02 | 1.3* |
| 14 | H26 | 0.114 | 0.149 | 0.13 | 0.05 | 2.9 |
| 15 | H29 | 0.111 | 0.063 | 0.09 | 0.01 | 0.4* |
| 16 | H30 | 0.099 | 0.092 | 0.10 | 0.02 | 0.9* |
| 17 | H32 (crystals and cell toxicity) | 0.087 | 0.055 | 0.07 | −0.01 | −0.5* |
| — | H33 | 0.086 | 0.125 | 0.11 | 0.03 | 1.4* |
| — | H34 | 0.117 | 0.120 | 0.12 | 0.04 | 2.2* |
| — | H35 | 0.103 | 0.090 | 0.10 | 0.02 | 0.9* |
| — | H36 | 0.105 | 0.128 | 0.12 | 0.04 | 2.1* |
| 17 | H37 | 0.099 | 0.100 | 0.10 | 0.02 | 1.1* |
| 8 | H38 | 0.103 | 0.159 | 0.13 | 0.05 | 2.9 |
| — | Blank | 0.072 | 0.086 | 0.08 | 0.00 | 0.0 |

TABLE 4B

Absorbance measurements and quantification of collagen in test samples H16, H21-23, H25-26, or H29-38 at 48 hours.

| SEQ ID NO | Peptides | $A_{560\,nm}$ | | Average | Average minus blank | Collagen (μg) |
|---|---|---|---|---|---|---|
| 9 | H16 | 0.065 | 0.064 | 0.06 | 0.00 | 0.3* |
| 10 | H21 | 0.089 | 0.126 | 0.11 | 0.05 | 2.9 |
| 11 | H22 | 0.102 | 0.087 | 0.09 | 0.03 | 2.1* |
| 12 | H23 | 0.093 | 0.082 | 0.09 | 0.03 | 1.7* |
| 13 | H25 | 0.059 | 0.084 | 0.07 | 0.01 | 0.7* |
| 14 | H26 | 0.081 | 0.153 | 0.12 | 0.06 | 3.5 |
| 15 | H29 | 0.086 | 0.094 | 0.09 | 0.03 | 1.9* |
| 16 | H30 | 0.083 | 0.101 | 0.09 | 0.03 | 2.0* |
| 17 | H32 (crystals and cell toxicity) | 0.088 | 0.072 | 0.08 | 0.02 | 1.2* |
| — | H33 | 0.096 | 0.092 | 0.09 | 0.03 | 2.1* |
| — | H34 | 0.076 | 0.155 | 0.12 | 0.06 | 3.4 |
| — | H35 | 0.120 | 0.074 | 0.10 | 0.04 | 2.3* |
| — | H36 | 0.154 | 0.082 | 0.12 | 0.06 | 3.6 |
| 17 | H37 | 0.078 | 0.114 | 0.10 | 0.04 | 2.2* |
| 8 | H38 | 0.123 | 0.089 | 0.11 | 0.05 | 2.8 |
| — | Blank | 0.106 | 0.0106 | 0.06 | 0.00 | 0.0 |

Because sample sizes were 100 μL, the concentration of collagen produced in each sample in micrograms per milliliter is determined by multiplying the amount of collagen detected by ten. The results of all samples tested are summarized in Table 5.

TABLE 5

Collagen synthesis induced by peptides

| SEQ ID NO | Name | Primary sequence | [Peptide] (µg/mL) | Collagen produced (µg/mL) | |
|---|---|---|---|---|---|
| | | | | 24 hrs | 48 hrs |
| 1 | H07 | PEGP | 50 | 0 | 54 |
| 2 | H08 | GFPG | 50 | 15 | 9 |
| 3 | H09 | GSPG | 50 | 35 | 0 |
| 4 | H10 | PGPR | 50 | 34 | 0 |
| — | H06 | H7, H8, H9, H10 (SEQ ID NOs: 1, 2, 3, 4) | 50 | 25 | 13 |
| 5 | H11 | GEPG | 50 | 45 | 21 |
| 6 | H12 | GAGP | 50 | 2 | 37 |
| 7 | H13 | GPPG | 50 | 18 | 2 |
| 8 | H14 | GEKG | 50 | 30 | 26 |
| 8 | H38 | GEKG | 0.3 | 29 | 28 |
| — | H15 | H11, H12, H13, H14 (SEQ ID NOs: 5, 6, 7, 8) | 50 | 25 | 43 |
| 9 | H16 | PEKP | 50 | 31 | 3 |
| 10 | H21 | PKGP | 50 | 25 | 29 |
| 11 | H22 | PGQP | 50 | 33 | 21 |
| 12 | H23 | PGTP | 50 | 1 | 17 |
| 13 | H25 | PMGP | 50 | 13 | 7 |
| 14 | H26 | PGPP | 50 | 29 | 35 |
| 15 | H29 | PQGP | 50 | 4 | 19 |
| 16 | H30 | PGNP | 50 | 9 | 20 |
| 17 | H32 | KTTKS (SEDERMA™ peptide) | 50 | na | 12 |
| 17 | H37 | KTTKS (SEDERMA™ peptide) | 0.3 | 11 | 22 |
| — | H33 | H16, H21, H22, H23 (SEQ ID NOs: 9, 10, 11, 12) | 50 | 14 | 21 |
| — | H34 | H22, H23, H25, H26 (SEQ ID NOs: 11, 12, 13, 14) | 50 | 22 | 34 |
| — | H35 | H25, H26, H29, H30 (SEQ ID NOs: 13, 14, 15, 16) | 50 | 9 | 23 |
| — | H36 | H7, H12, H11, H14 (SEQ ID NOs: 1, 6, 5, 8) | 50 | 21 | 36 |
| 18 | LL37 | LLGDFFRKSKEKIGKEFKRIVQRIDFLRNLVPRTES | 50 | 30 | 52 |

All tetrapeptides tested stimulated the production of soluble collagen. Of the sequences tested, GxxG tetrapeptides with a glutamic acid in position 2 best stimulate collagen at both 24 and 48 hour time-points. These sequences are H11 (GEPG; SEQ ID NO: 5), H14 (GEKG; SEQ ID NO: 8) and H38 (GEKG; SEQ ID NO: 8). The peptides were initially screened using a peptide concentration of 50 µg/mL. To survey the concentration effective for stimulating collagen production, H14 (SEQ ID NO: 8) was also tested at 0.3 µg/mL as H38. As shown in Table 5, H38-induced collagen stimulation was not diminished at the lower concentration, indicating that the maximal stimulating concentration of SEQ ID NO: 8 is at or below 0.3 µg/mL.

To test its efficacy, SEQ ID NO: 8 (H14 and H38) was compared to the peptide, LL37, (SEQ ID NO: 18) which is known to stimulate collagen production. Based on the amount of collagen released by fibroblasts in response to LL37, 25 µg/mL was considered a significant amount of collagen released due to contact with a tetrapeptide. SEQ ID NO: 8 induced about the same amount of collagen as LL37 (SEQ ID NO: 18) at 24 hours. Importantly, collagen produced as a result of contact with SEQ ID NO: 8 was substantially maintained for at least 48 hours. SEQ ID NO: 8 was also compared to a leading skin care peptide known to stimulate collagen production, KTTKS (SEQ ID NO: 17) (Katayama et. al., J. BIOL. CHEM. 288:9941-9944 (1983)). KTTKS is an ingredient in the product MATRIXYL™ (SEDERMA SAS, France). SEQ ID NO: 8 stimulated more collagen production than the KTTKS (SEQ ID NO: 17) peptide (Table 5) at 24 and 48 hours.

Example 4

Identification of Peptide Combinations that Synergistically Enhance Collagen Stimulation—COMBIKINES Heterogeneous populations of active tetrapeptides may stimulate collagen production at a higher level than homogenous samples of tetrapeptides. The components of the heterogeneous composition are called COMBIKINES™. COMBIKINES are a group of REPLIKINES combined to produce a greater or broader effect upon one or more target cell types. The peptides H11 (SEQ ID NO: 5), H12 (SEQ ID NO: 6), H13 (SEQ ID NO: 7), and H14 (SEQ ID NO: 8) were combined to a final concentration of 50 µg/mL and assayed using the same protocol as for the individual peptides. As expected, the result obtained at the 24 hour time point equaled the mean of the individual induction scores. The combination of peptides at 48 hours, however, induced collagen to a level of 43 µg/mL. Surprisingly, this amount was far in excess of the anticipated mean (21 µg/mL) of the four individual peptides (see Table 5). Thus, specific combinations of peptides may stimulate collagen production to a greater degree than the individual peptides at the same concentration. Further, tetrapeptides from a variety of ECM sources such as collagen, laminin, and elastin may produce enhanced induction of a variety of ECM proteins (see Tables 1 and 5).

Example 5

Cost-Effective COMBIKINE Manufacturing for Enhancing Stimulation of Collagen Production The high cost of peptide synthesis limits the feasibility of producing of heterogeneous compositions of bioactive peptides. The present invention greatly mitigates this limitation. Because the presently disclosed sequences have a commonality (e.g., a glycine or proline at both termini), a range of tetrapeptides varied at positions 2 and 3 can be synthesized in a single manufacturing run. The synthetic peptides can be made by any method known in the art. (Benoiton, N., *Chemistry of Peptide Synthesis*, CRC (2005)). During manufacture of the peptides, amino acid mixtures are added instead of homogenous samples. The chemistry for determining the correct ratios of amino acid concentrations added at the mixed positions to gain the desired ratio of resulting peptides has been described previously (Greenbaum et al., *Molecular and Cellular Proteomics* 1:60-68, 2002; Krstenansky et al., *Letters in Drug Design and Discovery* 1:6-13, 2004; both of which references are incorporated herein in their entirety). Using this methodology, a library of heterogeneous peptides can be made for nearly the same cost of synthesizing one peptide.

The application of this manufacturing process enables the cost-effective production of bioactive combikines. This is made possible by the unique composition of the disclosed tetrapeptides. The tetrapeptide mixtures are better suited for incorporation into topical use formulations than longer peptides. Because of their length, tetrapeptides have practical and chemical advantages over longer peptides, including the following: easier incorporation and dissolution into formulations, higher skin and pore permeability, and higher production yields with easier methods of manufacturing combinations of peptides. Although not required, the ideal formulations of tetrapeptides, singly or in combination, are formulations that maintain significant collagen production at 24 hours for up to 48 hours. More preferably, the formulations would induce synthesis of ECM for the entire 48 hour period such that more collagen is produced by 48 hours than at 24 hours. Although within the scope of the current invention, tetrapeptides that promote production of ECM proteins at 24 hours, but show diminished production at 48 hours, are less favored. In this regard, Table 6 shows the results of the currently disclosed peptides. Preferred peptides are in bold.

TABLE 6

Disclosed peptides

| SEQ ID NO | Peptides | Released collagen (µg /mL) 24 h | Released collagen (µg /mL) 48 h | Significant release of collagen at 24 h and 48 h | Increase in collagen release at 48 h v. 24 h | Decrease in collagen release at 48 h v. 24 h |
|---|---|---|---|---|---|---|
| 18 | LL37 | 30 | 52 | ✓ | ✓ | |
| — | H6 | 25 | 13 | | | |
| 1 | H7 | 0 | 54 | | ✓ | |
| 2 | H8 | 15 | 9 | | | |
| 3 | H9 | 35 | 0 | | | ✓ |
| 4 | H10 | 34 | 0 | | | ✓ |
| 5 | H11 | 45 | 21 | | | ✓ |
| 6 | H12 | 2 | 37 | | ✓ | |
| 7 | H13 | 18 | 2 | | | |
| 8 | H14 | 30 | 26 | ✓ | | |
| 8 | H38 | 29 | 28 | ✓ | | |
| — | H15 | 25 | 43 | ✓ | ✓ | |
| 9 | H16 | 31 | 3 | | | ✓ |
| 10 | H21 | 25 | 29 | ✓ | | |
| 11 | H22 | 33 | 21 | | | ✓ |
| 12 | H23 | 1 | 17 | | ✓ | |
| 13 | H25 | 13 | 7 | | | ✓ |
| 14 | H26 | 29 | 35 | ✓ | | |
| 15 | H29 | 4 | 19 | | ✓ | |
| 16 | H30 | 9 | 20 | | ✓ | |
| 17 | H32 (crystals and cell toxicity) | NA | 12 | | | |
| 17 | H37 | 11 | 22 | | ✓ | |
| — | H33 | 14 | 21 | | ✓ | |

TABLE 6-continued

Disclosed peptides

| SEQ ID NO | Peptides | Released collagen (μg/mL) 24 h | Released collagen (μg/mL) 48 h | Significant release of collagen at 24 h and 48 h | Increase in collagen release at 48 h v. 24 h | Decrease in collagen release at 48 h v. 24 h |
|---|---|---|---|---|---|---|
| — | H34 | 22 | 34 | | ✓ | |
| — | H35 | 9 | 23 | | ✓ | |
| — | H36 | 21 | 36 | | ✓ | |

Example 6

Collagen Stimulators also Serve as Multi-Effector Molecules Enhancing Skin Epithelial Cell Wound Closer Collagens are key components of all phases of wound healing. Stimulation of collagen production reflects that damage has occurred to the collagen network (e.g. by enzymes or physical destruction). Indeed, the total collapse of the collagen network in fact causes healing to take place. Therefore a collagen stimulator may also serve as a multi-effector molecule orchestrating certain matrix remodeling and enhancing wound healing.

Wound healing experiments were performed on monolayers of human skin epithelial cells (CRL-2592) plated onto 12-well plates. Cells were serum-starved for 24 hours before experimentation. Confluent monolayers of CRL-2592 were wounded using a P200 (200-μL) pipette tip. The wounds were washed and picture-documented prior to peptide treatment. Peptides were added to a final concentration from 20 to 40 μg/ml. Cells were kept in an incubator at 37° C., 5% $CO_2$, and 92% humidity, except when images were being captured for a short period at room temperature. Wound closure was followed at 6-hour and 10-hour time points. PBS-treated wounds were used as negative controls for comparison purposes.

TABLE 7

Effect of peptides on human skin epithelial wound closure in vitro

| | 0 hr | 6 hr | | 10 hr | |
|---|---|---|---|---|---|
| Compound | W-size* | W-size | % closure | W-size | % closure |
| PBS-1 | 36 | 29 | 19.40% | 21 | 41.70% |
| PBS-2 | 52 | 42 | 19.20% | 30 | 42.30% |
| SEQ ID NO: 14 | 25 | 12 | 52% | 2.75 | 89% |
| SEQ ID NO: 5 | 48 | 39 | 19% | 30 | 37.50% |

*W-size: wound size (arbitrary)

In vitro monolayer wound closure is a result of cell migration, which is important in many biological processes such as embryogenesis, angiogenesis, inflammatory reactions and wound repair. These processes are thought to be regulated by interactions with other cells, cytokines and ECM proteins. As shown in Table 7, SEQ ID NO: 14 significantly induces wound closure compared to the effects of PBS alone. Such activity is peptide-specific as well as cell type-specific since SEQ ID NO: 14 does not induce wound closure in a human skin fibroblast monolayer (data not shown). SEQ ID NO: 5 is also a collagen inducer, but does not enhance wound closure or epithelial cell migration to any great extent compared to the effects of PBS alone. The fact that SEQ ID NO: 14 induced cell migration or wound closure in a manner specific to skin epithelial cells (i.e. does not recruit fibroblasts) may add an advantage to using this peptide for skin care, since it is believed that the recruitment of large numbers of active fibroblasts to a wound site results in excess deposition and contraction of tissue resulting in scarring.

All of the compositions or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

What is claimed is:

1. A tetrapeptide capable of inducing production of extracellular matrix proteins, wherein the amino acid sequence of the tetrapeptide consists of SEQ ID NO: 1 having an acid or amidated carboxy-terminus.

2. A tetrapeptide capable of inducing production of extracellular matrix proteins, wherein the amino acid sequence of the tetrapeptide consists of SEQ ID NO:14 having an amidated carboxy-terminus.

3. A composition comprising a tetrapeptide of claim 1 and a pharmaceutically acceptable carrier.

4. A skincare composition comprising an emulsion of a tetrapeptide consisting of SEQ ID NO:1 or SEQ ID NO:14, and a dermatologically acceptable carrier.

5. The skincare composition of claim 4, wherein the dermatologically acceptable carrier is a lotion, cream, paste, or ointment.

6. The composition of claim 4, wherein the tetrapeptide is SEQ ID NO:1.

7. The composition of claim 4, wherein the tetrapeptide is SEQ ID NO:14.

8. The composition of claim 4, wherein the tetrapeptide is present in an effective concentration ranging from about 0.1 µg/ml to about 50 µg/mL.

9. The composition of claim 4 which further comprises a retinoid.

* * * * *

SEQUENCE LISTING

```
<160> NUMBER OF SEQ ID NOS: 46

<210> SEQ ID NO 1
<211> LENGTH: 4
<212> TYPE: PRT
<213> ORGANISM: Artificial
<220> FEATURE:
<223> OTHER INFORMATION: Synthetic Peptide H7

<400> SEQUENCE: 1
```

Pro Glu Gly Pro
1

<210> SEQ ID NO 2
<211> LENGTH: 4
<212> TYPE: PRT
<213> ORGANISM: Artificial
<220> FEATURE:
<223> OTHER INFORMATION: Synthetic Peptide H8

<400> SEQUENCE: 2

Gly Phe Pro Gly
1

<210> SEQ ID NO 3
<211> LENGTH: 4
<212> TYPE: PRT
<213> ORGANISM: Artificial
<220> FEATURE:
<223> OTHER INFORMATION: Synthetic Peptide H9

<400> SEQUENCE: 3

Gly Ser Pro Gly
1

<210> SEQ ID NO 4
<211> LENGTH: 4
<212> TYPE: PRT
<213> ORGANISM: Artificial
<220> FEATURE:
<223> OTHER INFORMATION: Synthetic Peptide H10

<400> SEQUENCE: 4

Pro Gly Pro Arg
1

<210> SEQ ID NO 5
<211> LENGTH: 4
<212> TYPE: PRT
<213> ORGANISM: Artificial
<220> FEATURE:
<223> OTHER INFORMATION: Synthetic Peptide H11

<400> SEQUENCE: 5

Gly Glu Pro Gly
1

<210> SEQ ID NO 6
<211> LENGTH: 4
<212> TYPE: PRT
<213> ORGANISM: Artificial
<220> FEATURE:
<223> OTHER INFORMATION: Synthetic Peptide H12

<400> SEQUENCE: 6

Gly Ala Gly Pro
1

<210> SEQ ID NO 7
<211> LENGTH: 4
<212> TYPE: PRT
<213> ORGANISM: Artificial
<220> FEATURE:
<223> OTHER INFORMATION: Synthetic Peptide H13

<400> SEQUENCE: 7

Gly Pro Pro Gly

```
<210> SEQ ID NO 8
<211> LENGTH: 4
<212> TYPE: PRT
<213> ORGANISM: Artificial
<220> FEATURE:
<223> OTHER INFORMATION: Synthetic Peptide H14

<400> SEQUENCE: 8

Gly Glu Lys Gly
1

<210> SEQ ID NO 9
<211> LENGTH: 4
<212> TYPE: PRT
<213> ORGANISM: Artificial
<220> FEATURE:
<223> OTHER INFORMATION: Synthetic Peptide H16

<400> SEQUENCE: 9

Pro Glu Lys Pro
1

<210> SEQ ID NO 10
<211> LENGTH: 4
<212> TYPE: PRT
<213> ORGANISM: Artificial
<220> FEATURE:
<223> OTHER INFORMATION: Synthetic Peptide H21

<400> SEQUENCE: 10

Pro Lys Gly Pro
1

<210> SEQ ID NO 11
<211> LENGTH: 4
<212> TYPE: PRT
<213> ORGANISM: Artificial
<220> FEATURE:
<223> OTHER INFORMATION: Synthetic Peptide H22

<400> SEQUENCE: 11

Pro Gly Gln Pro
1

<210> SEQ ID NO 12
<211> LENGTH: 4
<212> TYPE: PRT
<213> ORGANISM: Artificial
<220> FEATURE:
<223> OTHER INFORMATION: Synthetic Peptide H23

<400> SEQUENCE: 12

Pro Gly Thr Pro
1

<210> SEQ ID NO 13
<211> LENGTH: 4
<212> TYPE: PRT
<213> ORGANISM: Artificial
<220> FEATURE:
<223> OTHER INFORMATION: Synthetic Peptide H25

<400> SEQUENCE: 13

Pro Met Gly Pro
1
```

<210> SEQ ID NO 14
<211> LENGTH: 4
<212> TYPE: PRT
<213> ORGANISM: Artificial
<220> FEATURE:
<223> OTHER INFORMATION: Synthetic Peptide H26

<400> SEQUENCE: 14

Pro Gly Pro Pro
1

<210> SEQ ID NO 15
<211> LENGTH: 4
<212> TYPE: PRT
<213> ORGANISM: Artificial
<220> FEATURE:
<223> OTHER INFORMATION: Synthetic Peptide H29

<400> SEQUENCE: 15

Pro Gln Gly Pro
1

<210> SEQ ID NO 16
<211> LENGTH: 4
<212> TYPE: PRT
<213> ORGANISM: Artificial
<220> FEATURE:
<223> OTHER INFORMATION: Synthetic Peptide H30

<400> SEQUENCE: 16

Pro Gly Asn Pro
1

<210> SEQ ID NO 17
<211> LENGTH: 5
<212> TYPE: PRT
<213> ORGANISM: Artificial
<220> FEATURE:
<223> OTHER INFORMATION: Synthetic Peptide H32

<400> SEQUENCE: 17

Lys Thr Thr Lys Ser
1               5

<210> SEQ ID NO 18
<211> LENGTH: 36
<212> TYPE: PRT
<213> ORGANISM: Artificial
<220> FEATURE:
<223> OTHER INFORMATION: Peptide LL37

<400> SEQUENCE: 18

Leu Leu Gly Asp Phe Phe Arg Lys Ser Lys Glu Lys Ile Gly Lys Glu
1               5                   10                  15

Phe Lys Arg Ile Val Gln Arg Ile Asp Phe Leu Arg Asn Leu Val Pro
            20                  25                  30

Arg Thr Glu Ser
        35

<210> SEQ ID NO 19
<211> LENGTH: 4
<212> TYPE: PRT
<213> ORGANISM: Artificial
<220> FEATURE:
<223> OTHER INFORMATION: Synthetic Peptide

```
<400> SEQUENCE: 19

Gly Ala Ala Gly
1

<210> SEQ ID NO 20
<211> LENGTH: 4
<212> TYPE: PRT
<213> ORGANISM: Artificial
<220> FEATURE:
<223> OTHER INFORMATION: Synthetic Peptide

<400> SEQUENCE: 20

Gly Ala Lys Gly
1

<210> SEQ ID NO 21
<211> LENGTH: 4
<212> TYPE: PRT
<213> ORGANISM: Artificial
<220> FEATURE:
<223> OTHER INFORMATION: Synthetic Peptide

<400> SEQUENCE: 21

Gly Ala Pro Gly
1

<210> SEQ ID NO 22
<211> LENGTH: 4
<212> TYPE: PRT
<213> ORGANISM: Artificial
<220> FEATURE:
<223> OTHER INFORMATION: Synthetic Peptide

<400> SEQUENCE: 22

Gly Asp Lys Gly
1

<210> SEQ ID NO 23
<211> LENGTH: 4
<212> TYPE: PRT
<213> ORGANISM: Artificial
<220> FEATURE:
<223> OTHER INFORMATION: Synthetic Peptide

<400> SEQUENCE: 23

Gly Asp Arg Gly
1

<210> SEQ ID NO 24
<211> LENGTH: 4
<212> TYPE: PRT
<213> ORGANISM: Artificial
<220> FEATURE:
<223> OTHER INFORMATION: Synthetic Peptide

<400> SEQUENCE: 24

Gly Glu Arg Gly
1

<210> SEQ ID NO 25
<211> LENGTH: 4
<212> TYPE: PRT
<213> ORGANISM: Artificial
<220> FEATURE:
<223> OTHER INFORMATION: Synthetic Peptide
```

```
<400> SEQUENCE: 25

Gly Ile Pro Gly
1

<210> SEQ ID NO 26
<211> LENGTH: 4
<212> TYPE: PRT
<213> ORGANISM: Artificial
<220> FEATURE:
<223> OTHER INFORMATION: Synthetic Peptide

<400> SEQUENCE: 26

Gly Lys Asp Gly
1

<210> SEQ ID NO 27
<211> LENGTH: 4
<212> TYPE: PRT
<213> ORGANISM: Artificial
<220> FEATURE:
<223> OTHER INFORMATION: Synthetic Peptide

<400> SEQUENCE: 27

Gly Lys Pro Gly
1

<210> SEQ ID NO 28
<211> LENGTH: 4
<212> TYPE: PRT
<213> ORGANISM: Artificial
<220> FEATURE:
<223> OTHER INFORMATION: Synthetic Peptide

<400> SEQUENCE: 28

Gly Leu Lys Gly
1

<210> SEQ ID NO 29
<211> LENGTH: 4
<212> TYPE: PRT
<213> ORGANISM: Artificial
<220> FEATURE:
<223> OTHER INFORMATION: Synthetic Peptide

<400> SEQUENCE: 29

Gly Leu Pro Gly
1

<210> SEQ ID NO 30
<211> LENGTH: 4
<212> TYPE: PRT
<213> ORGANISM: Artificial
<220> FEATURE:
<223> OTHER INFORMATION: Synthetic Peptide

<400> SEQUENCE: 30

Gly Asn Pro Gly
1

<210> SEQ ID NO 31
<211> LENGTH: 4
<212> TYPE: PRT
<213> ORGANISM: Artificial
<220> FEATURE:
<223> OTHER INFORMATION: Synthetic Peptide

<400> SEQUENCE: 31
```

Gly Pro Ala Gly
1

<210> SEQ ID NO 32
<211> LENGTH: 4
<212> TYPE: PRT
<213> ORGANISM: Artificial
<220> FEATURE:
<223> OTHER INFORMATION: Synthetic Peptide

<400> SEQUENCE: 32

Gly Pro Lys Gly
1

<210> SEQ ID NO 33
<211> LENGTH: 4
<212> TYPE: PRT
<213> ORGANISM: Artificial
<220> FEATURE:
<223> OTHER INFORMATION: Synthetic Peptide

<400> SEQUENCE: 33

Gly Pro Gln Gly
1

<210> SEQ ID NO 34
<211> LENGTH: 4
<212> TYPE: PRT
<213> ORGANISM: Artificial
<220> FEATURE:
<223> OTHER INFORMATION: Synthetic Peptide

<400> SEQUENCE: 34

Gly Pro Arg Gly
1

<210> SEQ ID NO 35
<211> LENGTH: 4
<212> TYPE: PRT
<213> ORGANISM: Artificial
<220> FEATURE:
<223> OTHER INFORMATION: Synthetic Peptide

<400> SEQUENCE: 35

Gly Pro Ser Gly
1

<210> SEQ ID NO 36
<211> LENGTH: 4
<212> TYPE: PRT
<213> ORGANISM: Artificial
<220> FEATURE:
<223> OTHER INFORMATION: Synthetic Peptide

<400> SEQUENCE: 36

Gly Pro Thr Gly
1

<210> SEQ ID NO 37
<211> LENGTH: 4
<212> TYPE: PRT
<213> ORGANISM: Artificial
<220> FEATURE:
<223> OTHER INFORMATION: Synthetic Peptide

<400> SEQUENCE: 37

Gly Pro Val Gly
1

<210> SEQ ID NO 38
<211> LENGTH: 4
<212> TYPE: PRT
<213> ORGANISM: Artificial
<220> FEATURE:
<223> OTHER INFORMATION: Synthetic Peptide

<400> SEQUENCE: 38

Gly Gln Pro Gly
1

<210> SEQ ID NO 39
<211> LENGTH: 4
<212> TYPE: PRT
<213> ORGANISM: Artificial
<220> FEATURE:
<223> OTHER INFORMATION: Synthetic Peptide

<400> SEQUENCE: 39

Gly Arg Asp Gly
1

<210> SEQ ID NO 40
<211> LENGTH: 4
<212> TYPE: PRT
<213> ORGANISM: Artificial
<220> FEATURE:
<223> OTHER INFORMATION: Synthetic Peptide

<400> SEQUENCE: 40

Gly Arg Pro Gly
1

<210> SEQ ID NO 41
<211> LENGTH: 4
<212> TYPE: PRT
<213> ORGANISM: Artificial
<220> FEATURE:
<223> OTHER INFORMATION: Synthetic Peptide

<400> SEQUENCE: 41

Gly Thr Pro Gly
1

<210> SEQ ID NO 42
<211> LENGTH: 4
<212> TYPE: PRT
<213> ORGANISM: Artificial
<220> FEATURE:
<223> OTHER INFORMATION: Synthetic Peptide

<400> SEQUENCE: 42

Gly Val Lys Gly
1

<210> SEQ ID NO 43
<211> LENGTH: 4
<212> TYPE: PRT
<213> ORGANISM: Artificial
<220> FEATURE:
<223> OTHER INFORMATION: Synthetic Peptide

<400> SEQUENCE: 43

Gly Val Pro Gly

```
<210> SEQ ID NO 44
<211> LENGTH: 4
<212> TYPE: PRT
<213> ORGANISM: Artificial
<220> FEATURE:
<223> OTHER INFORMATION: Synthetic Peptide

<400> SEQUENCE: 44

Gly Tyr Pro Gly
1

<210> SEQ ID NO 45
<211> LENGTH: 1669
<212> TYPE: PRT
<213> ORGANISM: Homo sapiens

<400> SEQUENCE: 45

Met Gly Pro Arg Leu Ser Val Trp Leu Leu Leu Leu Pro Ala Ala Leu
1               5                   10                  15

Leu Leu His Glu Glu His Ser Arg Ala Ala Lys Gly Gly Cys Ala
            20                  25                  30

Gly Ser Gly Cys Gly Lys Cys Asp Cys His Gly Val Lys Gly Gln Lys
        35                  40                  45

Gly Glu Arg Gly Leu Pro Gly Leu Gln Gly Val Ile Gly Phe Pro Gly
    50                  55                  60

Met Gln Gly Pro Glu Gly Pro Gln Gly Pro Pro Gly Gln Lys Gly Asp
65                  70                  75                  80

Thr Gly Glu Pro Gly Leu Pro Gly Thr Lys Gly Thr Arg Gly Pro Pro
                85                  90                  95

Gly Ala Ser Gly Tyr Pro Gly Asn Pro Gly Leu Pro Gly Ile Pro Gly
            100                 105                 110

Gln Asp Gly Pro Pro Gly Pro Pro Gly Ile Pro Gly Cys Asn Gly Thr
        115                 120                 125

Lys Gly Glu Arg Gly Pro Leu Gly Pro Pro Gly Leu Pro Gly Phe Ala
    130                 135                 140

Gly Asn Pro Gly Pro Pro Gly Leu Pro Gly Met Lys Gly Asp Pro Gly
145                 150                 155                 160

Glu Ile Leu Gly His Val Pro Gly Met Leu Leu Lys Gly Glu Arg Gly
                165                 170                 175

Phe Pro Gly Ile Pro Gly Thr Pro Gly Pro Pro Gly Leu Pro Gly Leu
            180                 185                 190

Gln Gly Pro Val Gly Pro Pro Gly Phe Thr Gly Pro Pro Gly Pro Pro
        195                 200                 205

Gly Pro Pro Gly Pro Pro Gly Glu Lys Gly Gln Met Gly Leu Ser Phe
    210                 215                 220

Gln Gly Pro Lys Gly Asp Lys Gly Asp Gln Gly Val Ser Gly Pro Pro
225                 230                 235                 240

Gly Val Pro Gly Gln Ala Gln Val Gln Glu Lys Gly Asp Phe Ala Thr
                245                 250                 255

Lys Gly Glu Lys Gly Gln Lys Gly Glu Pro Gly Phe Gln Gly Met Pro
            260                 265                 270

Gly Val Gly Glu Lys Gly Glu Pro Gly Lys Pro Gly Pro Arg Gly Lys
        275                 280                 285

Pro Gly Lys Asp Gly Asp Lys Gly Glu Lys Gly Ser Pro Gly Phe Pro
    290                 295                 300
```

```
Gly Glu Pro Gly Tyr Pro Gly Leu Ile Gly Arg Gln Gly Pro Gln Gly
305                 310                 315                 320

Glu Lys Gly Glu Ala Gly Pro Pro Gly Pro Pro Gly Ile Val Ile Gly
                325                 330                 335

Thr Gly Pro Leu Gly Glu Lys Gly Glu Arg Gly Tyr Pro Gly Thr Pro
            340                 345                 350

Gly Pro Arg Gly Glu Pro Gly Pro Lys Gly Phe Pro Gly Leu Pro Gly
        355                 360                 365

Gln Pro Gly Pro Pro Gly Leu Pro Val Pro Gly Gln Ala Gly Ala Pro
    370                 375                 380

Gly Phe Pro Gly Glu Arg Gly Glu Lys Gly Asp Arg Gly Phe Pro Gly
385                 390                 395                 400

Thr Ser Leu Pro Gly Pro Ser Gly Arg Asp Gly Leu Pro Gly Pro Pro
                405                 410                 415

Gly Ser Pro Gly Pro Pro Gly Gln Pro Gly Tyr Thr Asn Gly Ile Val
            420                 425                 430

Glu Cys Gln Pro Gly Pro Pro Gly Asp Gln Gly Pro Pro Gly Ile Pro
        435                 440                 445

Gly Gln Pro Gly Phe Ile Gly Glu Ile Gly Glu Lys Gly Gln Lys Gly
    450                 455                 460

Glu Ser Cys Leu Ile Cys Asp Ile Asp Gly Tyr Arg Gly Pro Pro Gly
465                 470                 475                 480

Pro Gln Gly Pro Pro Gly Glu Ile Gly Phe Pro Gly Gln Pro Gly Ala
                485                 490                 495

Lys Gly Asp Arg Gly Leu Pro Gly Arg Asp Gly Val Ala Gly Val Pro
            500                 505                 510

Gly Pro Gln Gly Thr Pro Gly Leu Ile Gly Gln Pro Gly Ala Lys Gly
        515                 520                 525

Glu Pro Gly Glu Phe Tyr Phe Asp Leu Arg Leu Lys Gly Asp Lys Gly
    530                 535                 540

Asp Pro Gly Phe Pro Gly Gln Pro Gly Met Pro Gly Arg Ala Gly Ser
545                 550                 555                 560

Pro Gly Arg Asp Gly His Pro Gly Leu Pro Gly Pro Lys Gly Ser Pro
                565                 570                 575

Gly Ser Val Gly Leu Lys Gly Glu Arg Gly Pro Pro Gly Gly Val Gly
            580                 585                 590

Phe Pro Gly Ser Arg Gly Asp Thr Gly Pro Pro Gly Pro Pro Gly Tyr
        595                 600                 605

Gly Pro Ala Gly Pro Ile Gly Asp Lys Gly Gln Ala Gly Phe Pro Gly
    610                 615                 620

Gly Pro Gly Ser Pro Gly Leu Pro Gly Pro Lys Gly Glu Pro Gly Lys
625                 630                 635                 640

Ile Val Pro Leu Pro Gly Pro Pro Gly Ala Glu Gly Leu Pro Gly Ser
                645                 650                 655

Pro Gly Phe Pro Gly Pro Gln Gly Asp Arg Gly Phe Pro Gly Thr Pro
            660                 665                 670

Gly Arg Pro Gly Leu Pro Gly Glu Lys Gly Ala Val Gly Gln Pro Gly
        675                 680                 685

Ile Gly Phe Pro Gly Pro Pro Gly Pro Lys Gly Val Asp Gly Leu Pro
    690                 695                 700

Gly Asp Met Gly Pro Pro Gly Thr Pro Gly Arg Pro Gly Phe Asn Gly
705                 710                 715                 720
```

-continued

```
Leu Pro Gly Asn Pro Gly Val Gln Gly Gln Lys Gly Glu Pro Gly Val
                725                 730                 735

Gly Leu Pro Gly Leu Lys Gly Leu Pro Gly Leu Pro Gly Ile Pro Gly
            740                 745                 750

Thr Pro Gly Glu Lys Gly Ser Ile Gly Val Pro Gly Val Pro Gly Glu
            755                 760                 765

His Gly Ala Ile Gly Pro Pro Gly Leu Gln Gly Ile Arg Gly Glu Pro
            770                 775                 780

Gly Pro Pro Gly Leu Pro Gly Ser Val Gly Ser Pro Gly Val Pro Gly
785                 790                 795                 800

Ile Gly Pro Pro Gly Ala Arg Gly Pro Pro Gly Gly Gln Gly Pro Pro
                805                 810                 815

Gly Leu Ser Gly Pro Pro Gly Ile Lys Gly Glu Lys Gly Phe Pro Gly
            820                 825                 830

Phe Pro Gly Leu Asp Met Pro Gly Pro Lys Gly Asp Lys Gly Ala Gln
            835                 840                 845

Gly Leu Pro Gly Ile Thr Gly Gln Ser Gly Leu Pro Gly Leu Pro Gly
            850                 855                 860

Gln Gln Gly Ala Pro Gly Ile Pro Gly Phe Pro Gly Ser Lys Gly Glu
865                 870                 875                 880

Met Gly Val Met Gly Thr Pro Gly Gln Pro Gly Ser Pro Gly Pro Val
                885                 890                 895

Gly Ala Pro Gly Leu Pro Gly Glu Lys Gly Asp His Gly Phe Pro Gly
            900                 905                 910

Ser Ser Gly Pro Arg Gly Asp Pro Gly Leu Lys Gly Asp Lys Gly Asp
            915                 920                 925

Val Gly Leu Pro Gly Lys Pro Gly Ser Met Asp Lys Val Asp Met Gly
930                 935                 940

Ser Met Lys Gly Gln Lys Gly Asp Gln Gly Glu Lys Gly Gln Ile Gly
945                 950                 955                 960

Pro Ile Gly Glu Lys Gly Ser Arg Gly Asp Pro Gly Thr Pro Gly Val
                965                 970                 975

Pro Gly Lys Asp Gly Gln Ala Gly Gln Pro Gly Gln Pro Gly Pro Lys
            980                 985                 990

Gly Asp Pro Gly Ile Ser Gly Thr Pro Gly Ala Pro Gly Leu Pro Gly
            995                 1000                1005

Pro Lys Gly Ser Val Gly Gly Met Gly Leu Pro Gly Thr Pro Gly
        1010                1015                1020

Glu Lys Gly Val Pro Gly Ile Pro Gly Pro Gln Gly Ser Pro Gly
        1025                1030                1035

Leu Pro Gly Asp Lys Gly Ala Lys Gly Glu Lys Gly Gln Ala Gly
        1040                1045                1050

Pro Pro Gly Ile Gly Ile Pro Gly Leu Arg Gly Glu Lys Gly Asp
        1055                1060                1065

Gln Gly Ile Ala Gly Phe Pro Gly Ser Pro Gly Glu Lys Gly Glu
        1070                1075                1080

Lys Gly Ser Ile Gly Ile Pro Gly Met Pro Gly Ser Pro Gly Leu
        1085                1090                1095

Lys Gly Ser Pro Gly Ser Val Gly Tyr Pro Gly Ser Pro Gly Leu
        1100                1105                1110

Pro Gly Glu Lys Gly Asp Lys Gly Leu Pro Gly Leu Asp Gly Ile
        1115                1120                1125

Pro Gly Val Lys Gly Glu Ala Gly Leu Pro Gly Thr Pro Gly Pro
```

-continued

```
              1130                1135                1140

Thr Gly  Pro Ala Gly Gln  Lys Gly Glu Pro  Gly Ser Asp Gly  Ile
    1145                 1150                1155

Pro Gly  Ser Ala Gly Glu  Lys Gly Glu Pro  Gly Leu Pro Gly  Arg
    1160                 1165                1170

Gly Phe  Pro Gly Phe Pro  Gly Ala Lys Gly  Asp Lys Gly Ser  Lys
    1175                 1180                1185

Gly Glu  Val Gly Phe Pro  Gly Leu Ala Gly  Ser Pro Gly Ile  Pro
    1190                 1195                1200

Gly Ser  Lys Gly Glu Gln  Gly Phe Met Gly  Pro Gly Pro Gln
    1205                 1210                1215

Gly Gln  Pro Gly Leu Pro  Gly Ser Pro Gly  His Ala Thr Glu  Gly
    1220                 1225                1230

Pro Lys  Gly Asp Arg Gly  Pro Gln Gly Gln  Pro Gly Leu Pro  Gly
    1235                 1240                1245

Leu Pro  Gly Pro Met Gly  Pro Pro Gly Leu  Pro Gly Ile Asp  Gly
    1250                 1255                1260

Val Lys  Gly Asp Lys Gly  Asn Pro Gly Trp  Pro Gly Ala Pro  Gly
    1265                 1270                1275

Val Pro  Gly Pro Lys Gly  Asp Pro Gly Phe  Gln Gly Met Pro  Gly
    1280                 1285                1290

Ile Gly  Gly Ser Pro Gly  Ile Thr Gly Ser  Lys Gly Asp Met  Gly
    1295                 1300                1305

Pro Pro  Gly Val Pro Gly  Phe Gln Gly Pro  Lys Gly Leu Pro  Gly
    1310                 1315                1320

Leu Gln  Gly Ile Lys Gly  Asp Gln Gly Asp  Gln Gly Val Pro  Gly
    1325                 1330                1335

Ala Lys  Gly Leu Pro Gly  Pro Pro Gly Pro  Pro Gly Pro Tyr  Asp
    1340                 1345                1350

Ile Ile  Lys Gly Glu Pro  Gly Leu Pro Gly  Pro Glu Gly Pro  Pro
    1355                 1360                1365

Gly Leu  Lys Gly Leu Gln  Gly Leu Pro Gly  Pro Lys Gly Gln  Gln
    1370                 1375                1380

Gly Val  Thr Gly Leu Val  Gly Ile Pro Gly  Pro Pro Gly Ile  Pro
    1385                 1390                1395

Gly Phe  Asp Gly Ala Pro  Gly Gln Lys Gly  Glu Met Gly Pro  Ala
    1400                 1405                1410

Gly Pro  Thr Gly Pro Arg  Gly Phe Pro Gly  Pro Pro Gly Pro  Asp
    1415                 1420                1425

Gly Leu  Pro Gly Ser Met  Gly Pro Pro Gly  Thr Pro Ser Val  Asp
    1430                 1435                1440

His Gly  Phe Leu Val Thr  Arg His Ser Gln  Thr Ile Asp Asp  Pro
    1445                 1450                1455

Gln Cys  Pro Ser Gly Thr  Lys Ile Leu Tyr  His Gly Tyr Ser  Leu
    1460                 1465                1470

Leu Tyr  Val Gln Gly Asn  Glu Arg Ala His  Gly Gln Asp Leu  Gly
    1475                 1480                1485

Thr Ala  Gly Ser Cys Leu  Arg Lys Phe Ser  Thr Met Pro Phe  Leu
    1490                 1495                1500

Phe Cys  Asn Ile Asn Asn  Val Cys Asn Phe  Ala Ser Arg Asn  Asp
    1505                 1510                1515

Tyr Ser  Tyr Trp Leu Ser  Thr Pro Glu Pro  Met Pro Met Ser  Met
    1520                 1525                1530
```

-continued

```
Ala Pro Ile Thr Gly Glu Asn Ile Arg Pro Phe Ile Ser Arg Cys
1535                1540                1545

Ala Val Cys Glu Ala Pro Ala Met Val Met Ala Val His Ser Gln
1550                1555                1560

Thr Ile Gln Ile Pro Pro Cys Pro Ser Gly Trp Ser Ser Leu Trp
1565                1570                1575

Ile Gly Tyr Ser Phe Val Met His Thr Ser Ala Gly Ala Glu Gly
1580                1585                1590

Ser Gly Gln Ala Leu Ala Ser Pro Gly Ser Cys Leu Glu Glu Phe
1595                1600                1605

Arg Ser Ala Pro Phe Ile Glu Cys His Gly Arg Gly Thr Cys Asn
1610                1615                1620

Tyr Tyr Ala Asn Ala Tyr Ser Phe Trp Leu Ala Thr Ile Glu Arg
1625                1630                1635

Ser Glu Met Phe Lys Lys Pro Thr Pro Ser Thr Leu Lys Ala Gly
1640                1645                1650

Glu Leu Arg Thr His Val Ser Arg Cys Gln Val Cys Met Arg Arg
1655                1660                1665

Thr

<210> SEQ ID NO 46
<211> LENGTH: 1466
<212> TYPE: PRT
<213> ORGANISM: Homo sapiens

<400> SEQUENCE: 46

Met Met Ser Phe Val Gln Lys Gly Ser Trp Leu Leu Leu Ala Leu Leu
1               5                   10                  15

His Pro Thr Ile Ile Leu Ala Gln Gln Glu Ala Val Glu Gly Gly Cys
                20                  25                  30

Ser His Leu Gly Gln Ser Tyr Ala Asp Arg Asp Val Trp Lys Pro Glu
            35                  40                  45

Pro Cys Gln Ile Cys Val Cys Asp Ser Gly Ser Val Leu Cys Asp Asp
        50                  55                  60

Ile Ile Cys Asp Asp Gln Glu Leu Asp Cys Pro Asn Pro Glu Ile Pro
65                  70                  75                  80

Phe Gly Glu Cys Cys Ala Val Cys Pro Gln Pro Pro Thr Ala Pro Thr
                85                  90                  95

Arg Pro Pro Asn Gly Gln Gly Pro Gln Gly Pro Lys Gly Asp Pro Gly
            100                 105                 110

Pro Pro Gly Ile Pro Gly Arg Asn Gly Asp Pro Gly Ile Pro Gly Gln
        115                 120                 125

Pro Gly Ser Pro Gly Ser Pro Gly Pro Pro Gly Ile Cys Glu Ser Cys
    130                 135                 140

Pro Thr Gly Pro Gln Asn Tyr Ser Pro Gln Tyr Asp Ser Tyr Asp Val
145                 150                 155                 160

Lys Ser Gly Val Ala Val Gly Gly Leu Ala Gly Tyr Pro Gly Pro Ala
                165                 170                 175

Gly Pro Pro Gly Pro Pro Gly Pro Pro Gly Thr Ser Gly His Pro Gly
            180                 185                 190

Ser Pro Gly Ser Pro Gly Tyr Gln Gly Pro Pro Gly Glu Pro Gly Gln
        195                 200                 205

Ala Gly Pro Ser Gly Pro Pro Gly Pro Pro Gly Ala Ile Gly Pro Ser
    210                 215                 220
```

```
Gly Pro Ala Gly Lys Asp Gly Glu Ser Gly Arg Pro Gly Arg Pro Gly
225                 230                 235                 240

Glu Arg Gly Leu Pro Gly Pro Pro Gly Ile Lys Gly Pro Ala Gly Ile
            245                 250                 255

Pro Gly Phe Pro Gly Met Lys Gly His Arg Gly Phe Asp Gly Arg Asn
            260                 265                 270

Gly Glu Lys Gly Glu Thr Gly Ala Pro Gly Leu Lys Gly Glu Asn Gly
            275                 280                 285

Leu Pro Gly Glu Asn Gly Ala Pro Gly Pro Met Gly Pro Arg Gly Ala
290                 295                 300

Pro Gly Glu Arg Gly Arg Pro Gly Leu Pro Gly Ala Ala Gly Ala Arg
305                 310                 315                 320

Gly Asn Asp Gly Ala Arg Gly Ser Asp Gly Gln Pro Gly Pro Pro Gly
                325                 330                 335

Pro Pro Gly Thr Ala Gly Phe Pro Gly Ser Pro Gly Ala Lys Gly Glu
            340                 345                 350

Val Gly Pro Ala Gly Ser Pro Gly Ser Asn Gly Ala Pro Gly Gln Arg
            355                 360                 365

Gly Glu Pro Gly Pro Gln Gly His Ala Gly Ala Gln Gly Pro Pro Gly
370                 375                 380

Pro Pro Gly Ile Asn Gly Ser Pro Gly Gly Lys Gly Glu Met Gly Pro
385                 390                 395                 400

Ala Gly Ile Pro Gly Ala Pro Gly Leu Met Gly Ala Arg Gly Pro Pro
            405                 410                 415

Gly Pro Ala Gly Ala Asn Gly Ala Pro Gly Leu Arg Gly Ala Gly Gly
            420                 425                 430

Glu Pro Gly Lys Asn Gly Ala Lys Gly Glu Pro Gly Pro Arg Gly Glu
            435                 440                 445

Arg Gly Glu Ala Gly Ile Pro Gly Val Pro Gly Ala Lys Gly Glu Asp
450                 455                 460

Gly Lys Asp Gly Ser Pro Gly Glu Pro Gly Ala Asn Gly Leu Pro Gly
465                 470                 475                 480

Ala Ala Gly Glu Arg Gly Ala Pro Gly Phe Arg Gly Pro Ala Gly Pro
            485                 490                 495

Asn Gly Ile Pro Gly Glu Lys Gly Pro Ala Gly Glu Arg Gly Ala Pro
            500                 505                 510

Gly Pro Ala Gly Pro Arg Gly Ala Ala Gly Glu Pro Gly Arg Asp Gly
            515                 520                 525

Val Pro Gly Gly Pro Gly Met Arg Gly Met Pro Gly Ser Pro Gly Gly
            530                 535                 540

Pro Gly Ser Asp Gly Lys Pro Gly Pro Pro Gly Ser Gln Gly Glu Ser
545                 550                 555                 560

Gly Arg Pro Gly Pro Pro Gly Pro Ser Gly Pro Arg Gly Gln Pro Gly
            565                 570                 575

Val Met Gly Phe Pro Gly Pro Lys Gly Asn Asp Gly Ala Pro Gly Lys
            580                 585                 590

Asn Gly Glu Arg Gly Gly Pro Gly Gly Pro Gly Pro Gln Gly Pro Pro
            595                 600                 605

Gly Lys Asn Gly Glu Thr Gly Pro Gln Gly Pro Pro Gly Pro Thr Gly
            610                 615                 620

Pro Gly Gly Asp Lys Gly Asp Thr Gly Pro Pro Gly Pro Gln Gly Leu
625                 630                 635                 640
```

```
Gln Gly Leu Pro Gly Thr Gly Gly Pro Gly Glu Asn Gly Lys Pro
                645                 650                 655

Gly Glu Pro Gly Pro Lys Gly Asp Ala Gly Ala Pro Gly Ala Pro Gly
            660                 665                 670

Gly Lys Gly Asp Ala Gly Ala Pro Gly Glu Arg Gly Pro Pro Gly Leu
        675                 680                 685

Ala Gly Ala Pro Gly Leu Arg Gly Gly Ala Gly Pro Pro Gly Pro Glu
    690                 695                 700

Gly Gly Lys Gly Ala Ala Gly Pro Pro Gly Pro Pro Gly Ala Ala Gly
705                 710                 715                 720

Thr Pro Gly Leu Gln Gly Met Pro Gly Glu Arg Gly Gly Leu Gly Ser
                725                 730                 735

Pro Gly Pro Lys Gly Asp Lys Gly Glu Pro Gly Gly Pro Gly Ala Asp
            740                 745                 750

Gly Val Pro Gly Lys Asp Gly Pro Arg Gly Pro Thr Gly Pro Ile Gly
        755                 760                 765

Pro Pro Gly Pro Ala Gly Gln Pro Gly Asp Lys Gly Glu Gly Gly Ala
    770                 775                 780

Pro Gly Leu Pro Gly Ile Ala Gly Pro Arg Gly Ser Pro Gly Glu Arg
785                 790                 795                 800

Gly Glu Thr Gly Pro Pro Gly Pro Ala Gly Phe Pro Gly Ala Pro Gly
                805                 810                 815

Gln Asn Gly Glu Pro Gly Gly Lys Gly Glu Arg Gly Ala Pro Gly Glu
            820                 825                 830

Lys Gly Glu Gly Gly Pro Pro Gly Val Ala Gly Pro Pro Gly Gly Ser
        835                 840                 845

Gly Pro Ala Gly Pro Pro Gly Pro Gln Gly Val Lys Gly Glu Arg Gly
    850                 855                 860

Ser Pro Gly Gly Pro Gly Ala Ala Gly Phe Pro Gly Ala Arg Gly Leu
865                 870                 875                 880

Pro Gly Pro Pro Gly Ser Asn Gly Asn Pro Gly Pro Pro Gly Pro Ser
                885                 890                 895

Gly Ser Pro Gly Lys Asp Gly Pro Pro Gly Pro Ala Gly Asn Thr Gly
            900                 905                 910

Ala Pro Gly Ser Pro Gly Val Ser Gly Pro Lys Gly Asp Ala Gly Gln
        915                 920                 925

Pro Gly Glu Lys Gly Ser Pro Gly Ala Gln Gly Pro Pro Gly Ala Pro
    930                 935                 940

Gly Pro Leu Gly Ile Ala Gly Ile Thr Gly Ala Arg Gly Leu Ala Gly
945                 950                 955                 960

Pro Pro Gly Met Pro Gly Pro Arg Gly Ser Pro Gly Pro Gln Gly Val
                965                 970                 975

Lys Gly Glu Ser Gly Lys Pro Gly Ala Asn Gly Leu Ser Gly Glu Arg
            980                 985                 990

Gly Pro Pro Gly Pro Gln Gly Leu Pro Gly Leu Ala Gly Thr Ala Gly
        995                 1000                1005

Glu Pro Gly Arg Asp Gly Asn Pro Gly Ser Asp Gly Leu Pro Gly
    1010                1015                1020

Arg Asp Gly Ser Pro Gly Gly Lys Gly Asp Arg Gly Glu Asn Gly
    1025                1030                1035

Ser Pro Gly Ala Pro Gly Ala Pro Gly His Pro Gly Pro Pro Gly
    1040                1045                1050

Pro Val Gly Pro Ala Gly Lys Ser Gly Asp Arg Gly Glu Ser Gly
```

-continued

```
            1055                1060                1065
Pro Ala Gly Pro Ala Gly Ala Pro Gly Pro Ala Gly Ser Arg Gly
        1070                1075                1080
Ala Pro Gly Pro Gln Gly Pro Arg Gly Asp Lys Gly Glu Thr Gly
        1085                1090                1095
Glu Arg Gly Ala Ala Gly Ile Lys Gly His Arg Gly Phe Pro Gly
        1100                1105                1110
Asn Pro Gly Ala Pro Gly Ser Pro Gly Pro Ala Gly Gln Gln Gly
        1115                1120                1125
Ala Ile Gly Ser Pro Gly Pro Ala Gly Pro Arg Gly Pro Val Gly
        1130                1135                1140
Pro Ser Gly Pro Pro Gly Lys Asp Gly Thr Ser Gly His Pro Gly
        1145                1150                1155
Pro Ile Gly Pro Pro Gly Pro Arg Gly Asn Arg Gly Glu Arg Gly
        1160                1165                1170
Ser Glu Gly Ser Pro Gly His Pro Gly Gln Pro Gly Pro Pro Gly
        1175                1180                1185
Pro Pro Gly Ala Pro Gly Pro Cys Cys Gly Gly Val Gly Ala Ala
        1190                1195                1200
Ala Ile Ala Gly Ile Gly Gly Glu Lys Ala Gly Gly Phe Ala Pro
        1205                1210                1215
Tyr Tyr Gly Asp Glu Pro Met Asp Phe Lys Ile Asn Thr Asp Glu
        1220                1225                1230
Ile Met Thr Ser Leu Lys Ser Val Asn Gly Gln Ile Glu Ser Leu
        1235                1240                1245
Ile Ser Pro Asp Gly Ser Arg Lys Asn Pro Ala Arg Asn Cys Arg
        1250                1255                1260
Asp Leu Lys Phe Cys His Pro Glu Leu Lys Ser Gly Glu Tyr Trp
        1265                1270                1275
Val Asp Pro Asn Gln Gly Cys Lys Leu Asp Ala Ile Lys Val Phe
        1280                1285                1290
Cys Asn Met Glu Thr Gly Glu Thr Cys Ile Ser Ala Asn Pro Leu
        1295                1300                1305
Asn Val Pro Arg Lys His Trp Trp Thr Asp Ser Ala Glu Lys
        1310                1315                1320
Lys His Val Trp Phe Gly Glu Ser Met Asp Gly Gly Phe Gln Phe
        1325                1330                1335
Ser Tyr Gly Asn Pro Glu Leu Pro Glu Asp Val Leu Asp Val Gln
        1340                1345                1350
Leu Ala Phe Leu Arg Leu Leu Ser Ser Arg Ala Ser Gln Asn Ile
        1355                1360                1365
Thr Tyr His Cys Lys Asn Ser Ile Ala Tyr Met Asp Gln Ala Ser
        1370                1375                1380
Gly Asn Val Lys Lys Ala Leu Lys Leu Met Gly Ser Asn Glu Gly
        1385                1390                1395
Glu Phe Lys Ala Glu Gly Asn Ser Lys Phe Thr Tyr Thr Val Leu
        1400                1405                1410
Glu Asp Gly Cys Thr Lys His Thr Gly Glu Trp Ser Lys Thr Val
        1415                1420                1425
Phe Glu Tyr Arg Thr Arg Lys Ala Val Arg Leu Pro Ile Val Asp
        1430                1435                1440
Ile Ala Pro Tyr Asp Ile Gly Gly Pro Asp Gln Glu Phe Gly Val
        1445                1450                1455
```

```
Asp Val Gly Pro Val Cys Phe Leu
    1460            1465
```